(12) United States Patent
Kimani Mwangi et al.

(10) Patent No.: US 8,567,407 B1
(45) Date of Patent: *Oct. 29, 2013

(54) INTERNAL PRESSURE THERAPY APPARATUS

(75) Inventors: Anthony P. Kimani Mwangi, Atlanta, GA (US); Elijah Charles Walker, Sliver Spring, MD (US)

(73) Assignee: Dreamscape Medical LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,607

(22) Filed: Feb. 28, 2012

Related U.S. Application Data

(63) Continuation of application No. 13/405,928, filed on Feb. 27, 2012, which is a continuation-in-part of application No. 12/419,413, filed on Apr. 7, 2009, now Pat. No. 8,122,891.

(60) Provisional application No. 61/123,306, filed on Apr. 7, 2008, provisional application No. 61/489,095, filed on May 23, 2011.

(51) Int. Cl.
*A61F 5/56* (2006.01)
*A61H 31/00* (2006.01)

(52) U.S. Cl.
USPC .......................................... 128/848; 601/43

(58) Field of Classification Search
USPC ............ 128/202.28, 200.24, 202.29, 203.11, 128/204.23, 204.18, DIG. 23; 600/41, 43, 600/44; 601/39, 41–44, 6–11
See application file for complete search history.

(56) References Cited

U.S. PATENT DOCUMENTS

| | | | |
|---|---|---|---|
| 4,366,815 A | 1/1983 | Broomes | |
| 4,715,367 A | 12/1987 | Crossley | |
| 5,076,259 A * | 12/1991 | Hayek | 601/44 |
| 5,222,478 A * | 6/1993 | Scarberry et al. | 601/44 |
| 5,343,878 A | 9/1994 | Scarberry et al. | |
| 5,592,938 A | 1/1997 | Scarberry et al. | |
| 5,672,148 A | 9/1997 | Maunier | |
| 6,123,071 A | 9/2000 | Berthon-Jones et al. | |
| 7,743,768 B2 | 6/2010 | Ho et al. | |
| 2003/0167018 A1 | 9/2003 | Wyckoff | |
| 2005/0098176 A1 | 5/2005 | Hoffrichter | |
| 2006/0069357 A1 | 3/2006 | Marasco | |
| 2006/0266369 A1 | 11/2006 | Atkinson et al. | |
| 2007/0221231 A1 | 9/2007 | Macken | |
| 2007/0277818 A1 | 12/2007 | Chen | |
| 2009/0177124 A1 | 7/2009 | Silwa et al. | |

FOREIGN PATENT DOCUMENTS

WO 9634586 A1 11/1996

\* cited by examiner

*Primary Examiner* — Patricia Bianco
*Assistant Examiner* — Tarla Patel
(74) *Attorney, Agent, or Firm* — Hunton & Williams LLP

(57) ABSTRACT

A hydraulic device that includes a membrane-covered walled enclosure that enables control of pressure against a body part to be controlled through desired fluid addition or removal from the enclosure. Through pressure control of the membrane a desired traction force is applied to prevent injuries or therapeutically treat a wide variety of medical conditions, including respiratory, cardiovascular, musculoskeletal and skin disorders.

9 Claims, 16 Drawing Sheets

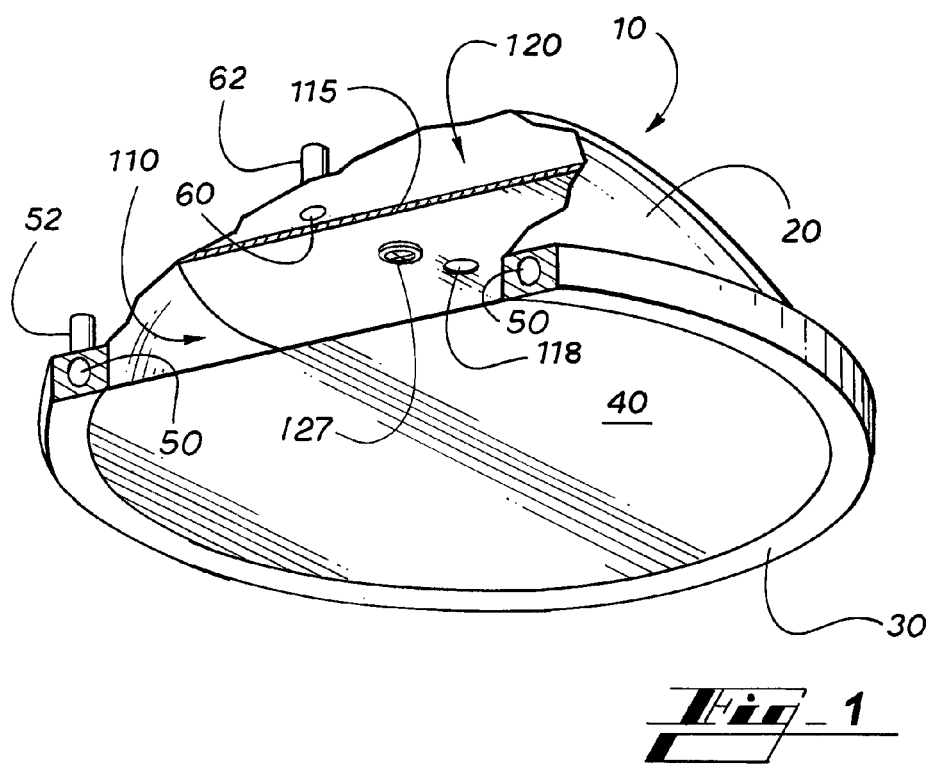
Fig_1

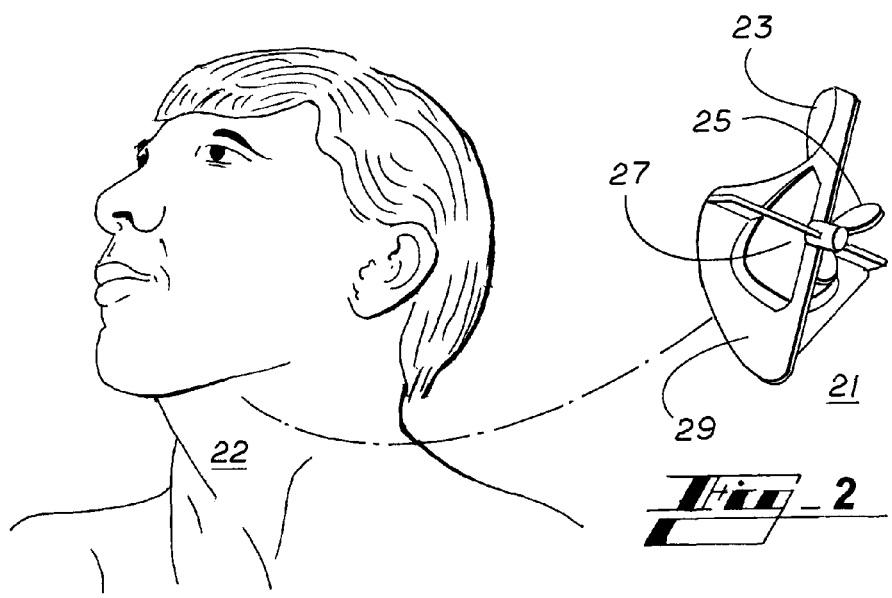
Fig_2
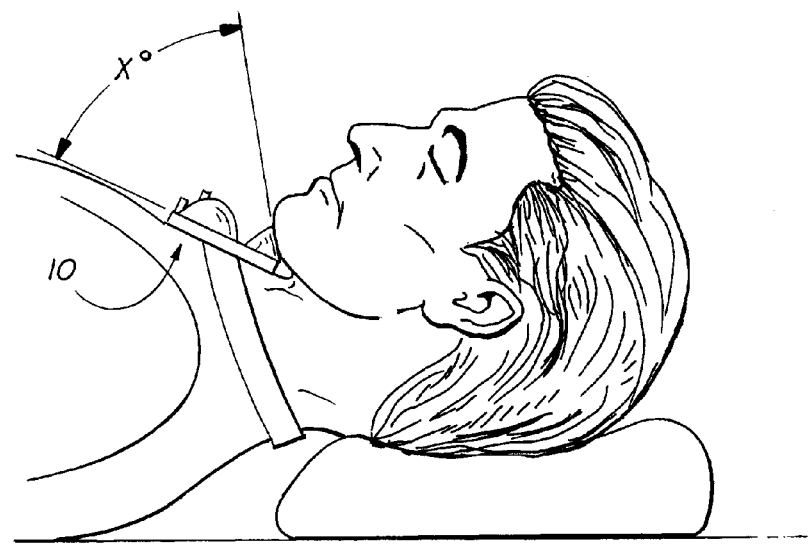
Fig_3

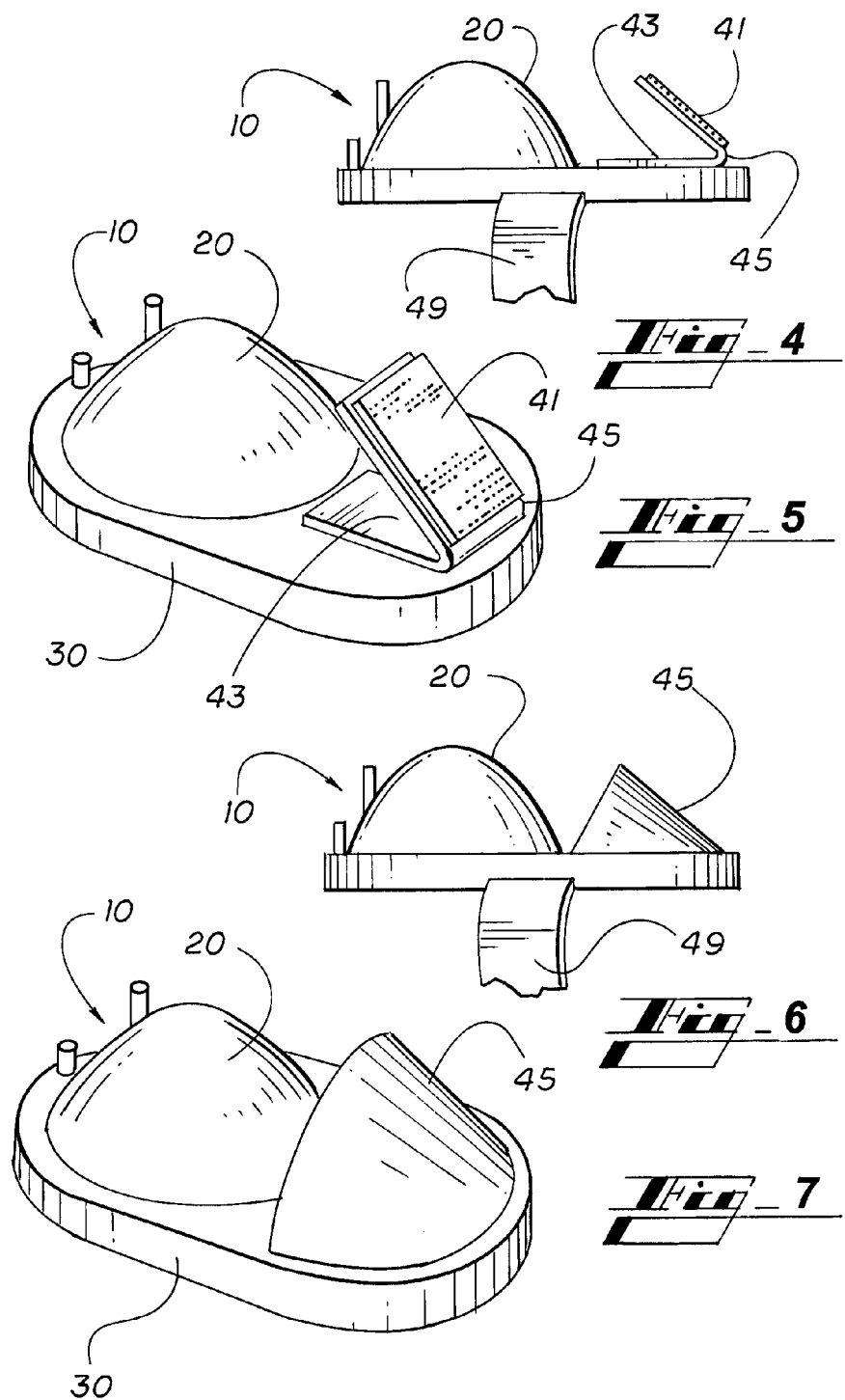

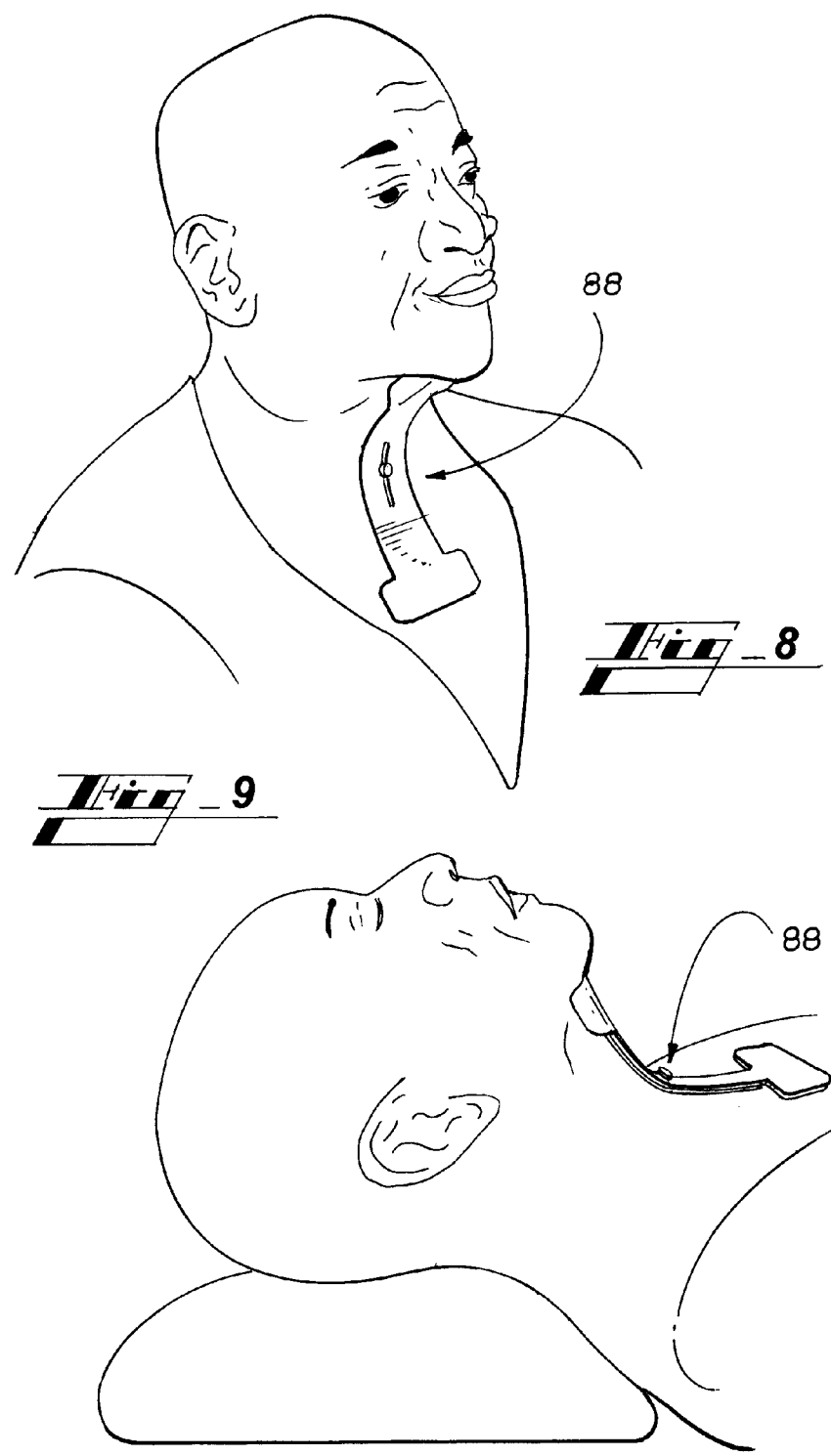
Fig_8
Fig_9

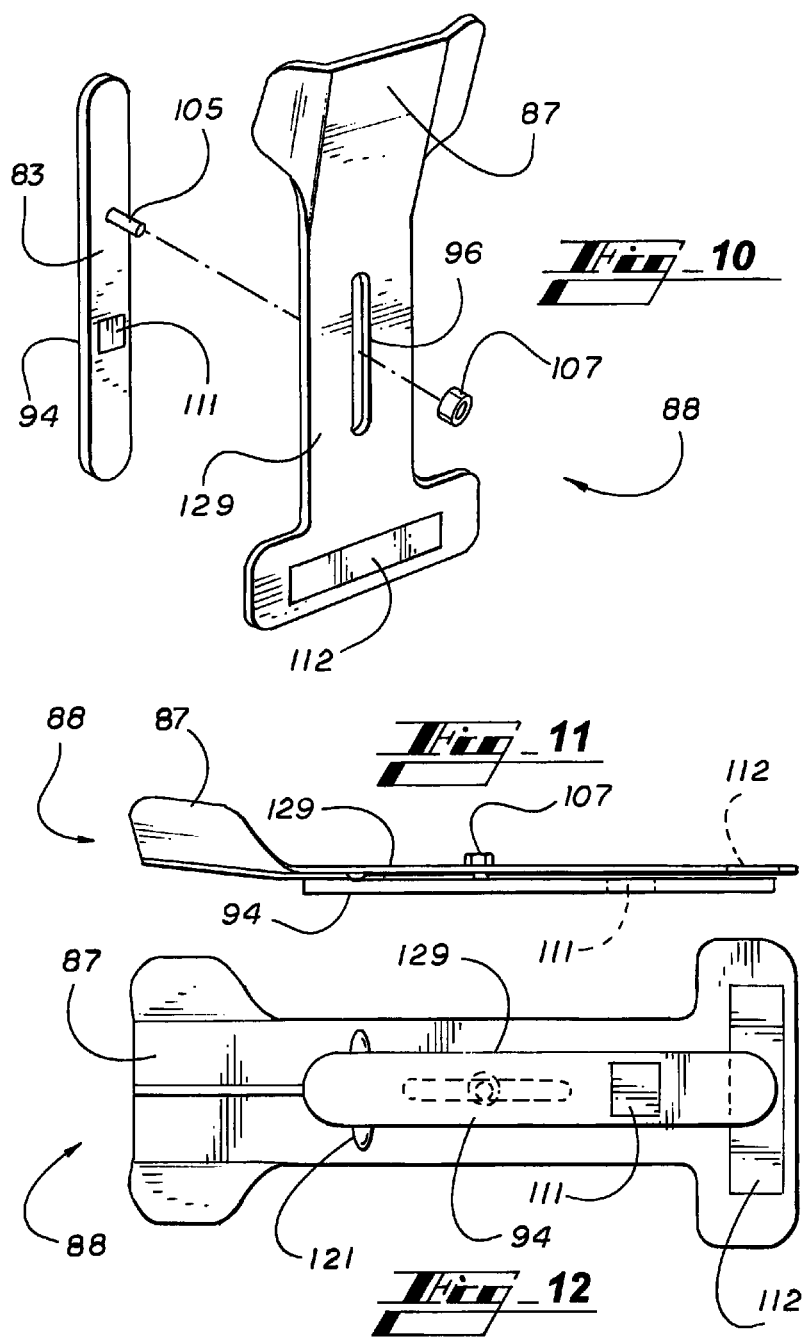

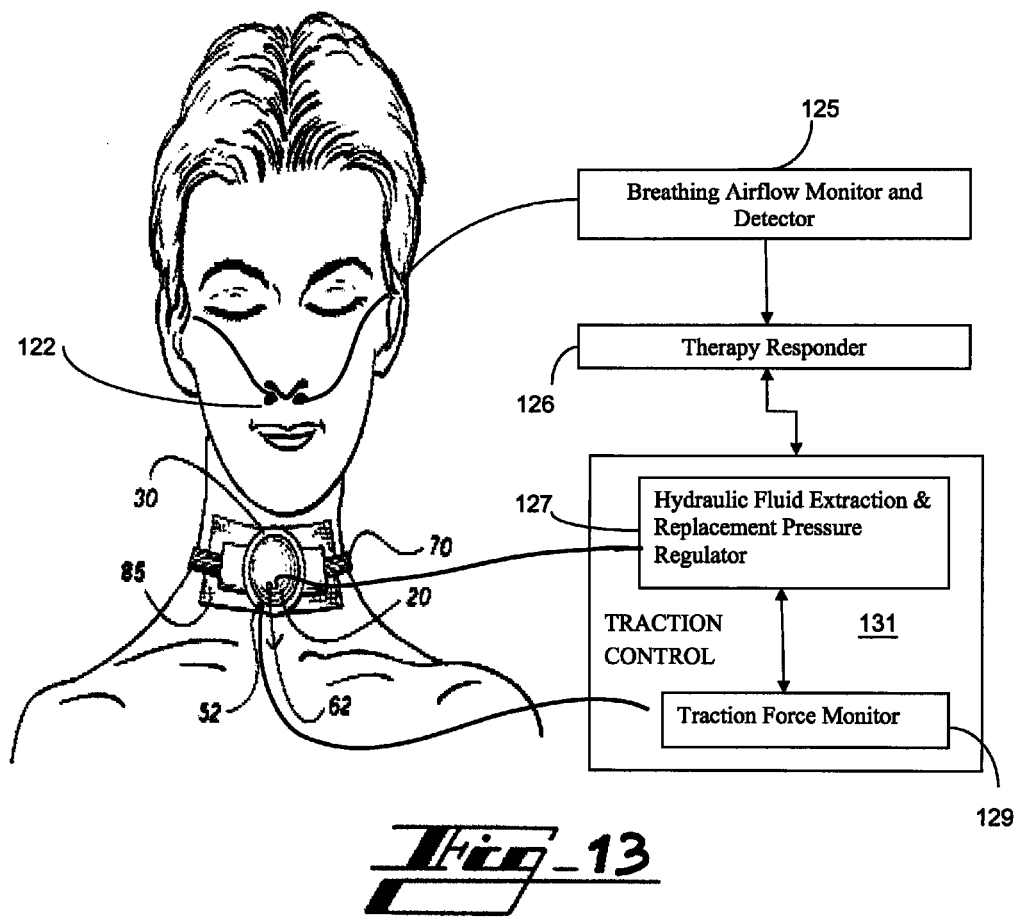
Fig_13

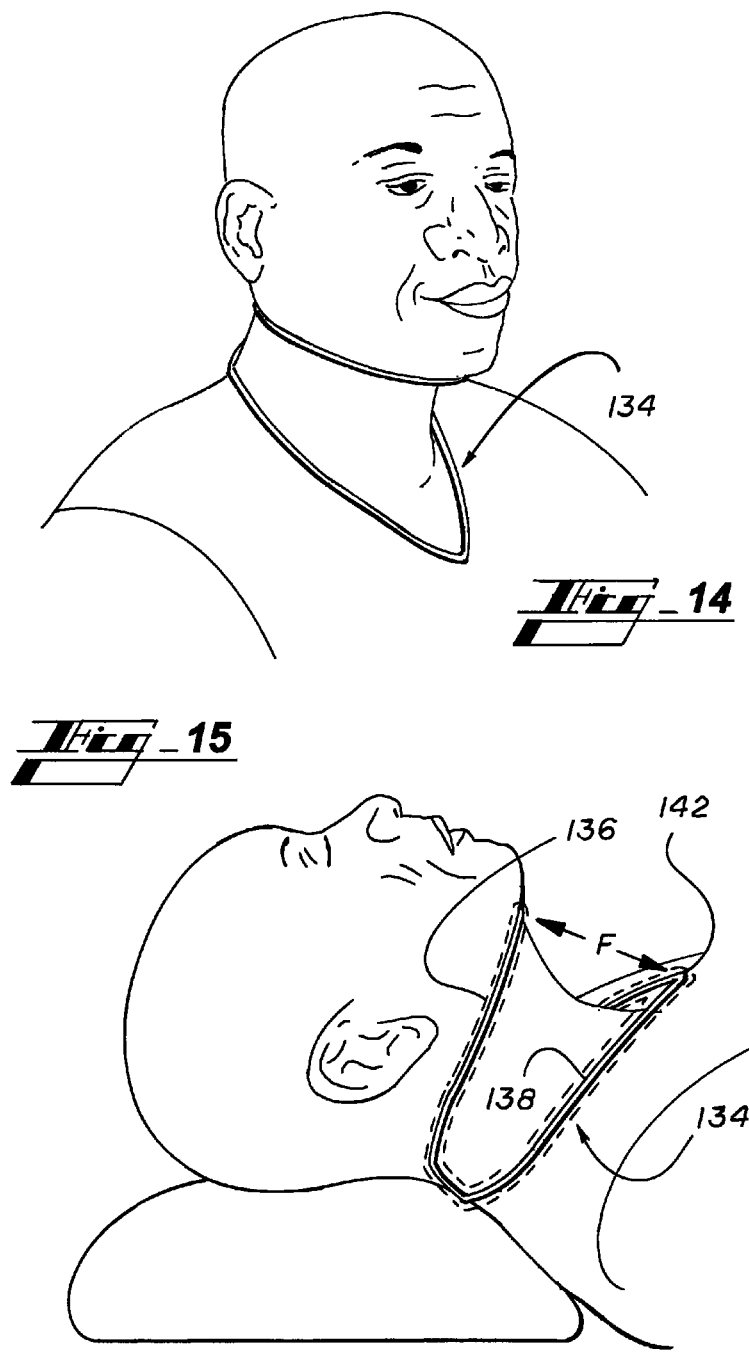

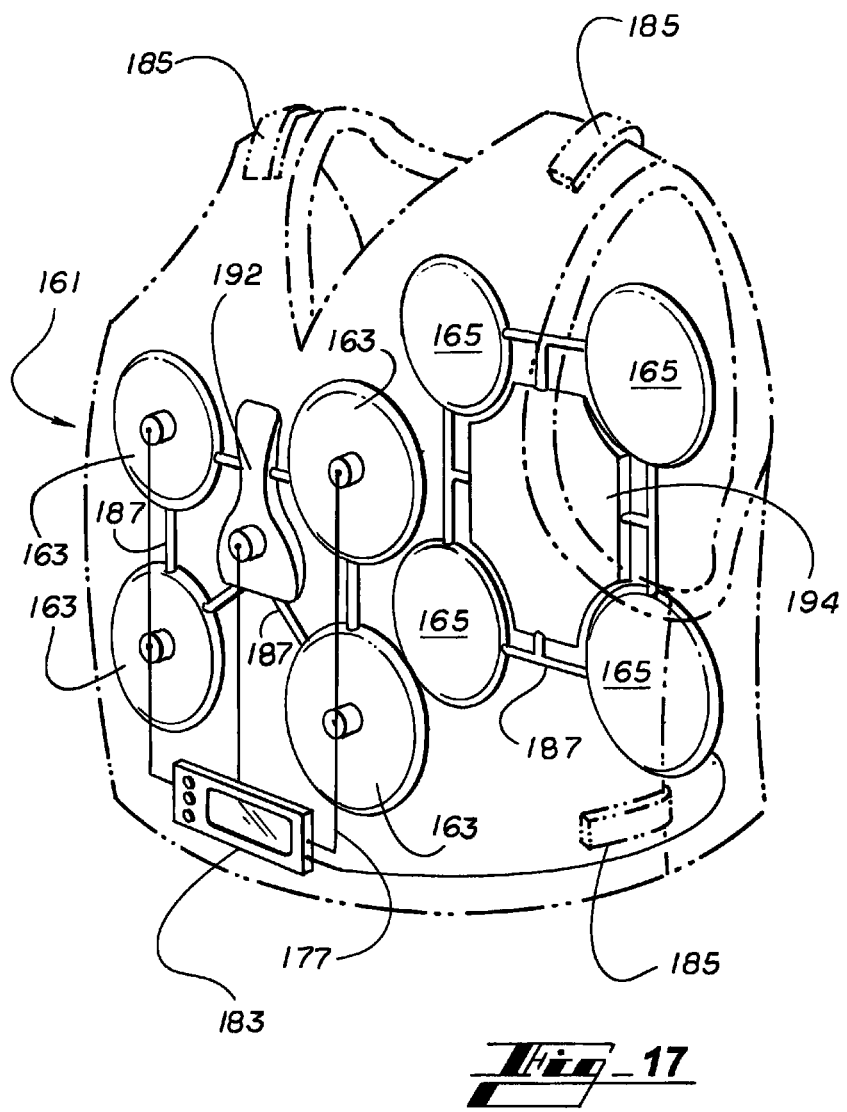

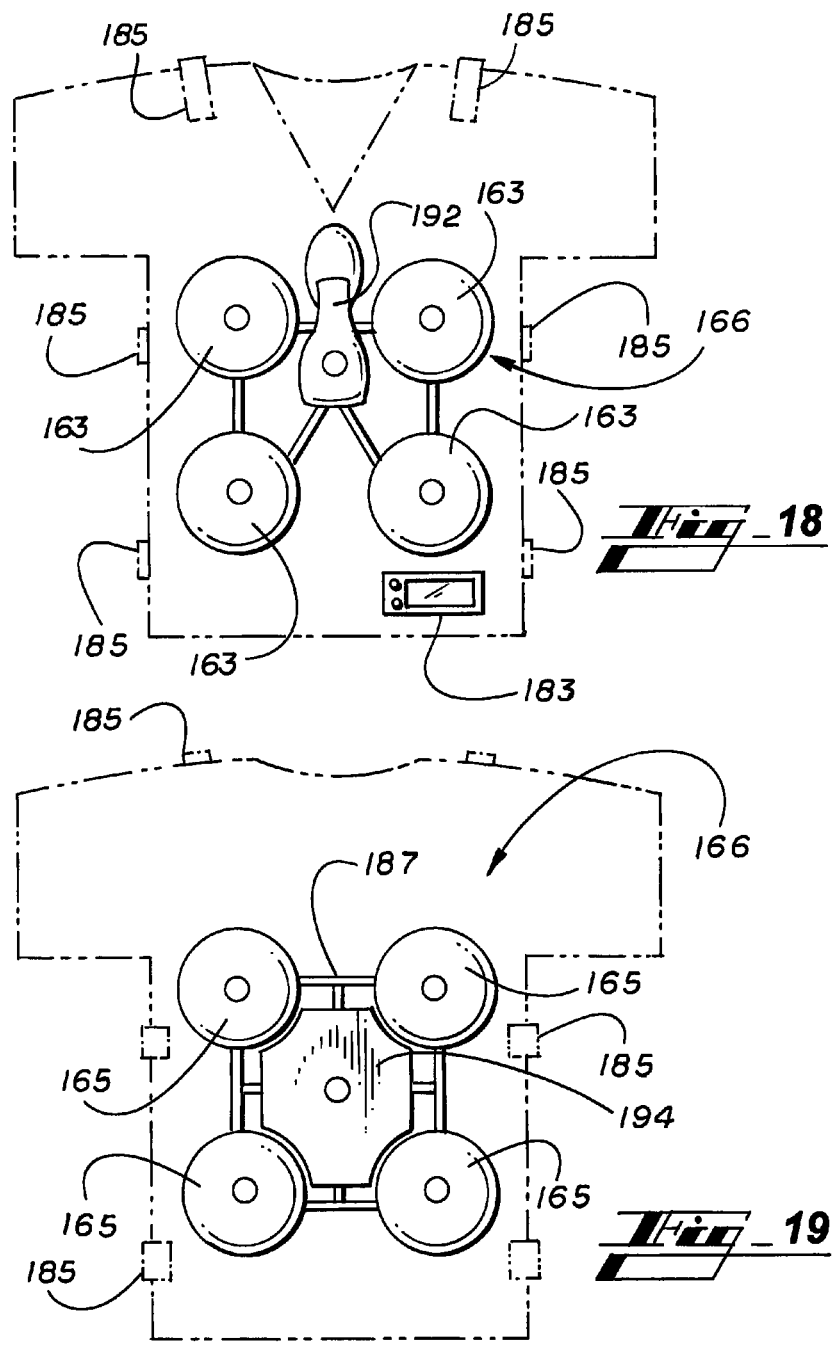

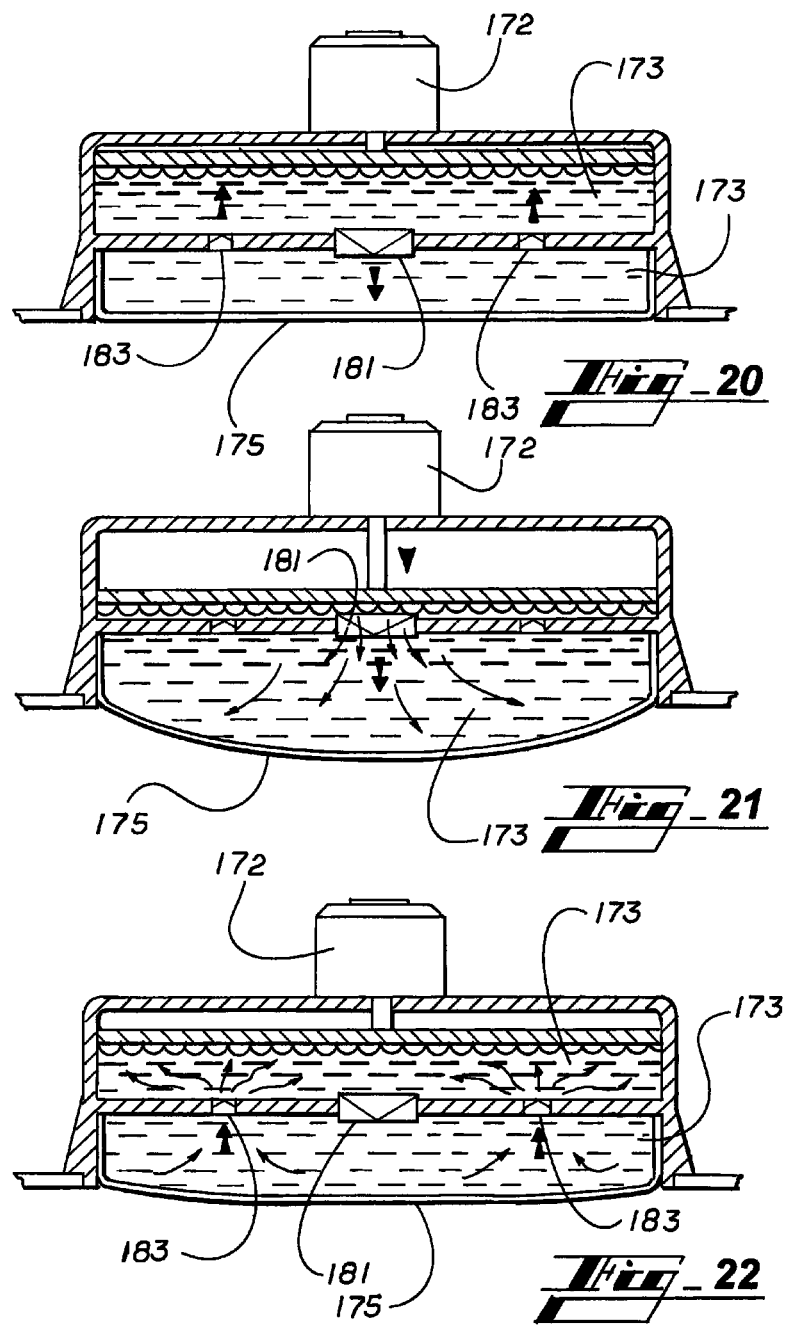

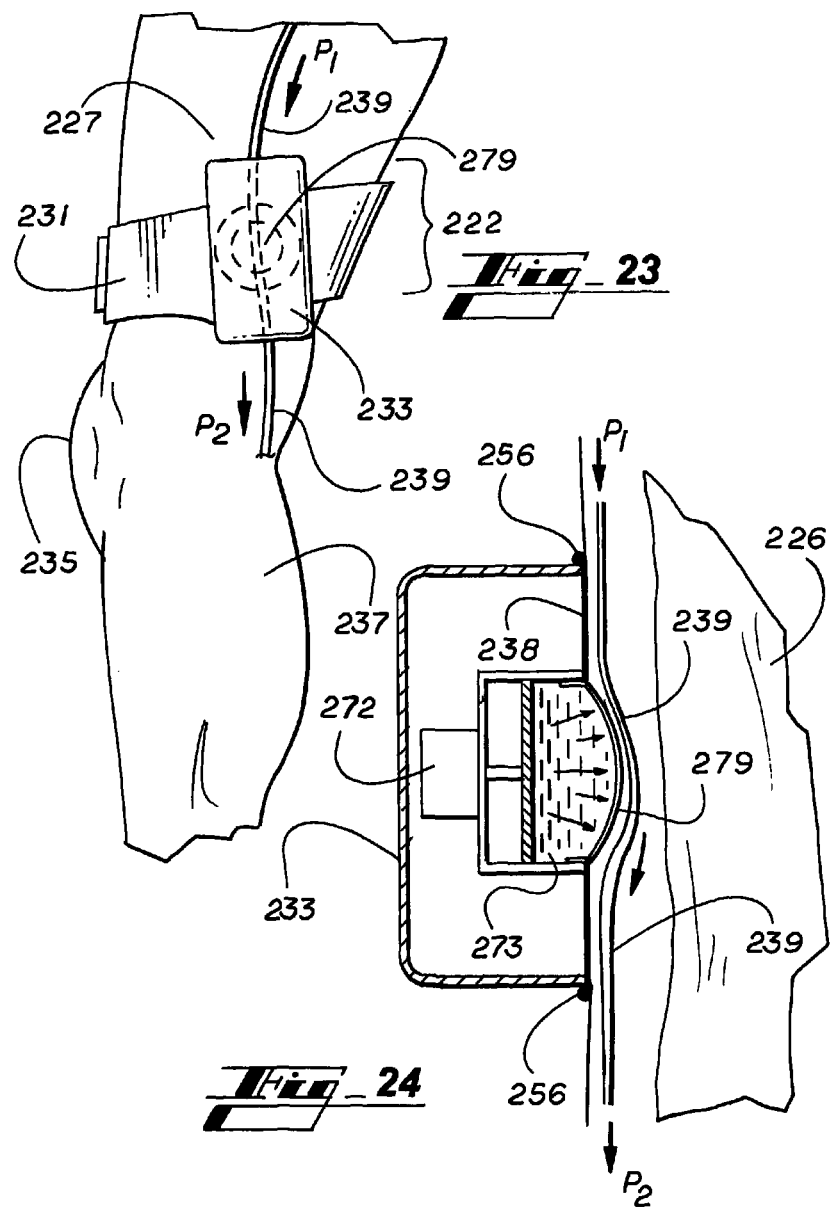

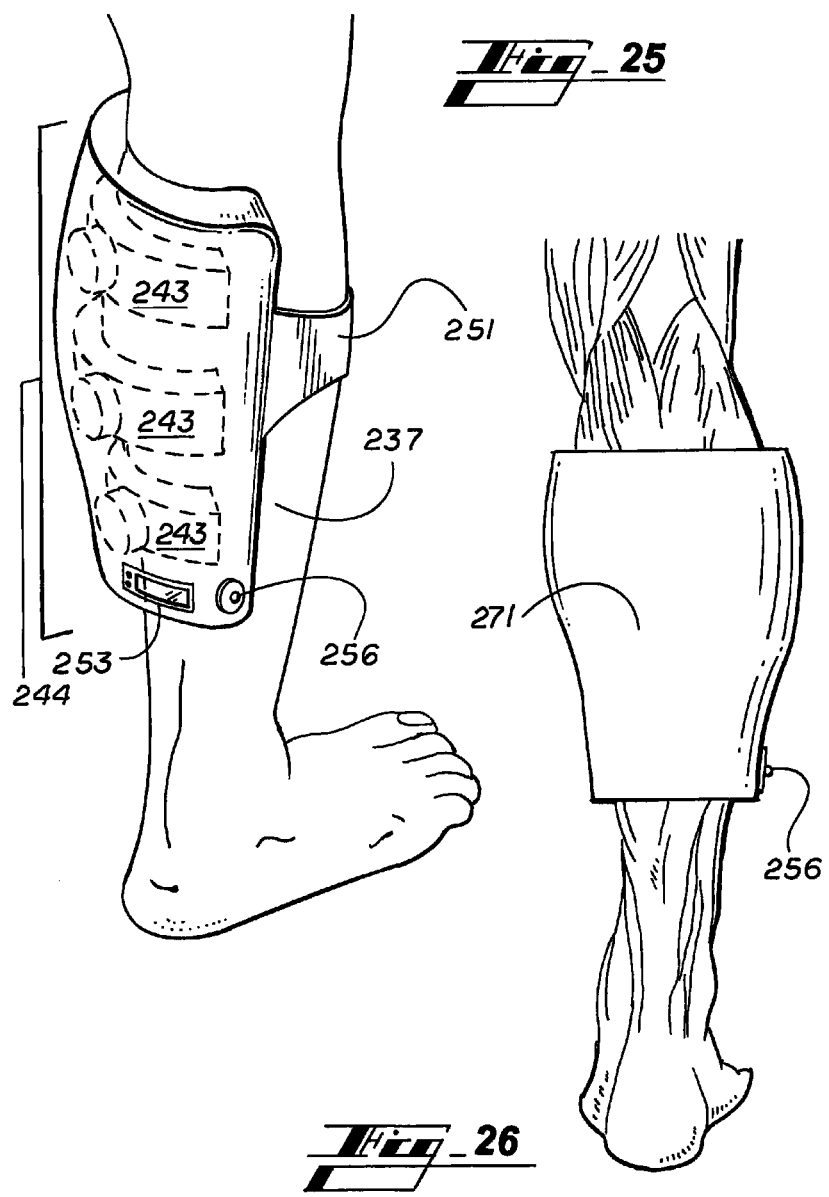

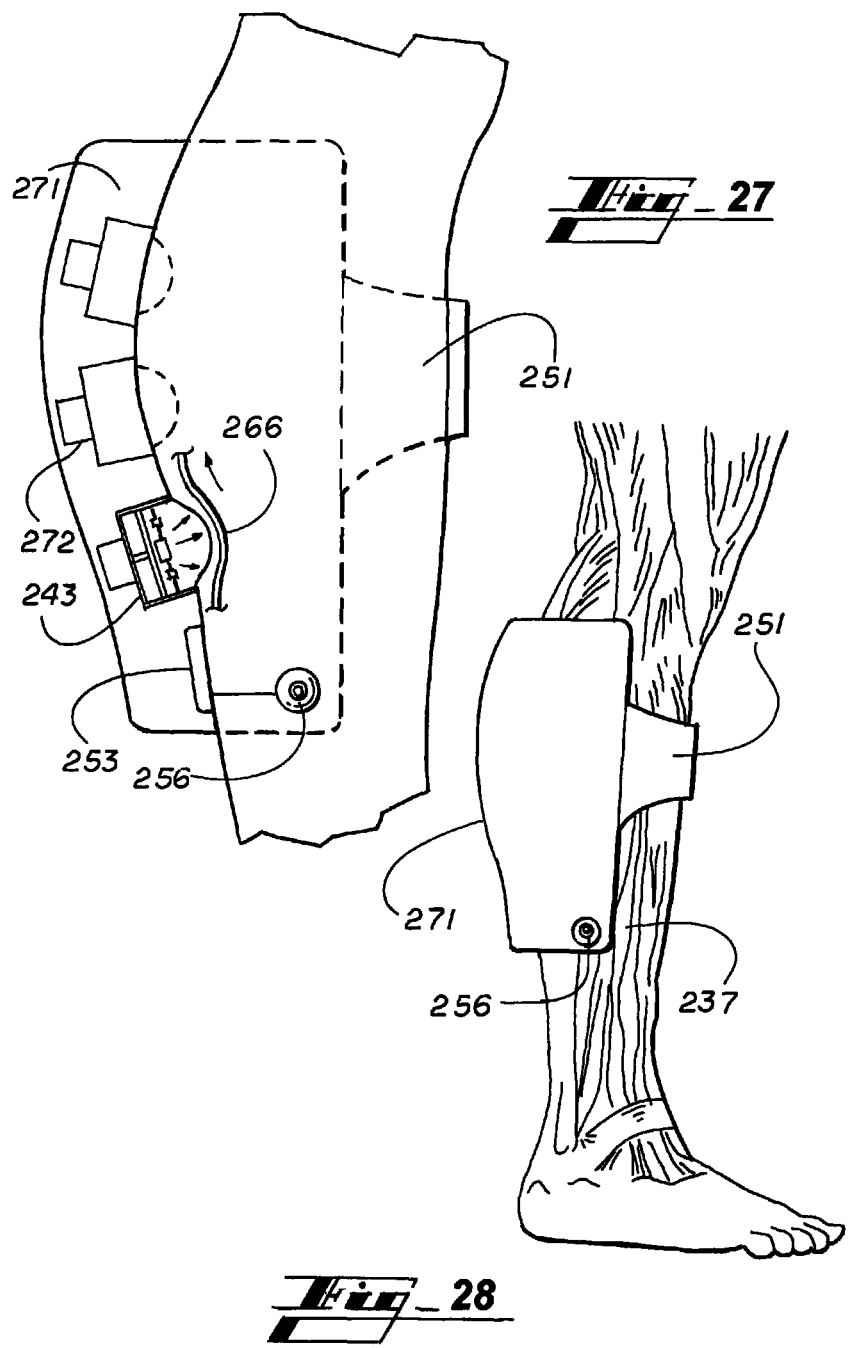

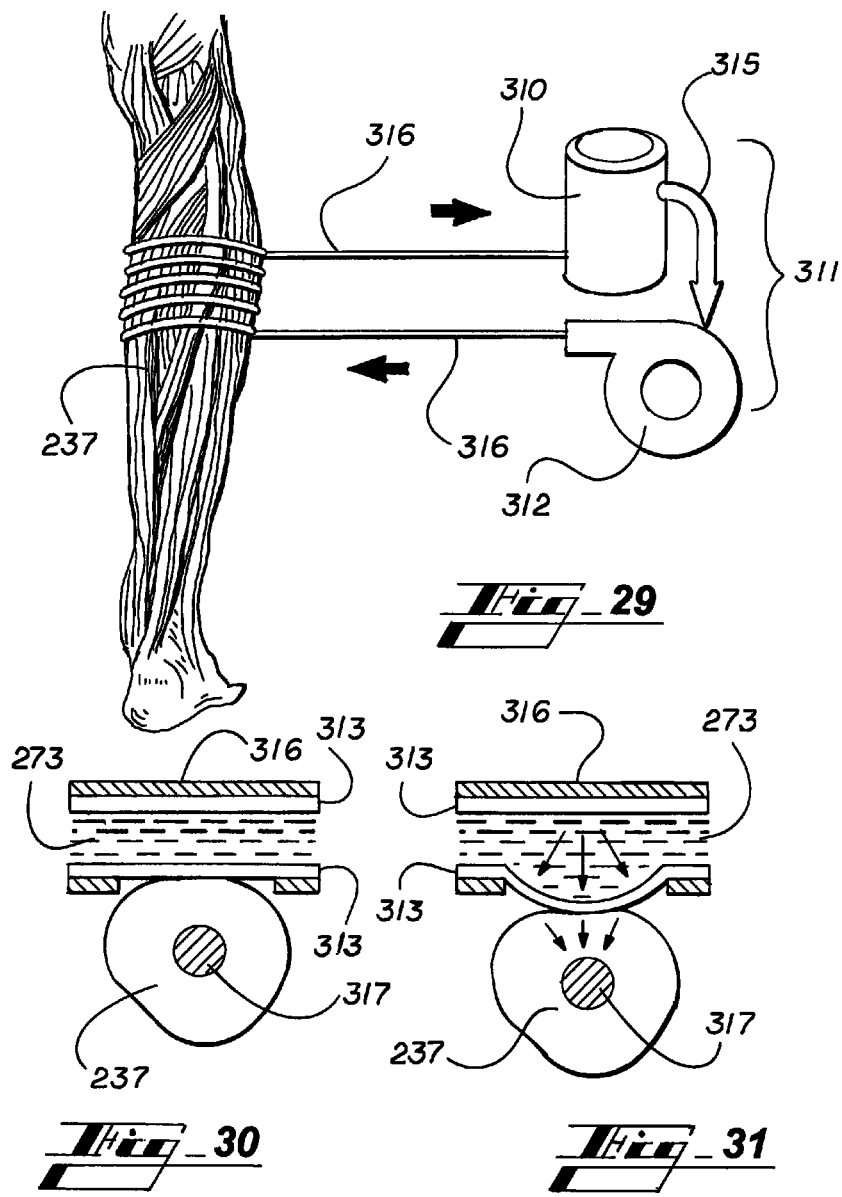

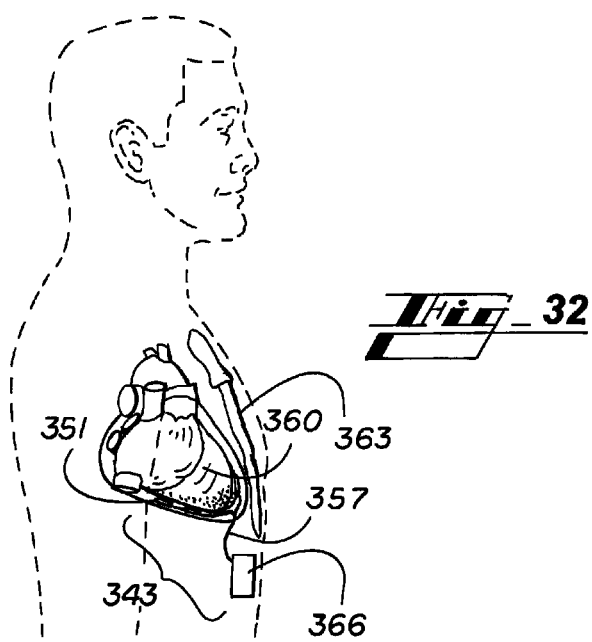
Fig_32
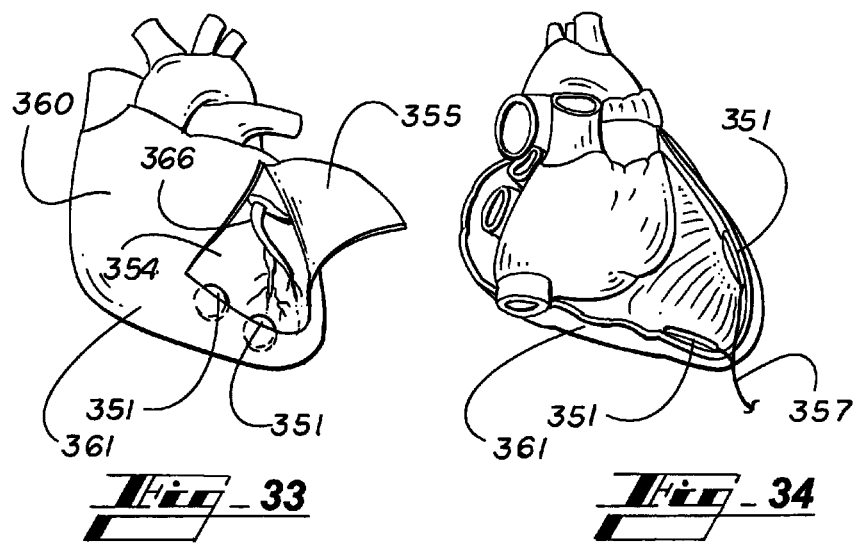
Fig_33
Fig_34

INTERNAL PRESSURE THERAPY APPARATUS

CROSS-REFERENCE TO RELATED APPLICATIONS

This application is a continuation of U.S. application Ser. No. 13/405,928 filed Feb. 27, 2012, which is a continuation-in-part of U.S. application Ser. No. 12/419,413, filed Apr. 7, 2009, now U.S. Pat. No. 8,122,891, which claims the benefit of priority of U.S. provisional application No. 61/123,306, filed Apr. 7, 2008, and further claims the benefit of priority of U.S. provisional application No. 61/489,095, filed May 23, 2011, that are all incorporated herein by reference in their entirety.

BACKGROUND

Hydraulic pressure has the benefits of performing work efficiently, lending itself to miniaturization, quiet operation, and the options of manual as well as electronic operation.

The present invention relates generally to application of hydraulic pressure for medical treatment. Therapeutic application of hydraulic pressure to the body in the form of negative (suction), positive (tension) or traction (sliding) pressure can be used to treat a wide range of conditions, including, for example, cardiovascular, respiratory, muscular, skeletal, lymphatic and skin conditions. In some embodiments, the invention can be adapted for sleep breathing therapy, and more specifically, to provide apparatuses and methods for treating sleep disordered breathing, such as snoring, and obstructive sleep apnea, with hydraulic suction or traction used to open the upper airway.

The present invention also describes a novel traction method for externally opening the upper airway by manipulating the anatomic relationships between the skin and soft tissues of the neck and upper chest, and the hyoid bone located in the throat and directly connected to the tongue.

Obstructive sleep apnea (OSA) is a common but under-diagnosed breathing disorder affecting 1 out of 5 adults in the United States. It is caused by airway collapse and blockage when the tongue falls back in the throat and the airway walls compress the upper air passage during sleep. This causes snoring and chronic sleep deprivation that manifests as daytime fatigue, reduced mental ability, driving and work related accidents, and lower overall productivity. The silent health consequences in those with moderate or severe OSA can be serious (high blood pressure, diabetes, acid reflux, blood clots) or even life threatening (miscarriage, stroke, heart attack, or sudden death from heart rhythm abnormalities). Habitual snoring occurs in 44% of men and 28% of women aged 30 to 60 in the United States, and is responsible for significant sleep disruption for bed partners of loud snorers.

The health consequences can be serious or even life threatening in those with severe OSA. Low blood and tissue oxygen levels caused by cessation of respiration trigger the release of stress hormones like cortisol and adrenaline. These chemicals cause harmful surges in blood pressure, heart rate and blood sugar. Repetitive cycles of this process may lead to a stroke, heart attack or sudden death.

Recent human clinical research has demonstrated that the critical pressure at which the upper airway collapses and limits flow to a maximal level ($P_{CRIT}$) is a measure of upper airway collapsibility and depends on the stability of the walls defining the upper airway as well as the surrounding pressure. $P_{CRIT}$ is defined as the pressure inside the upper airway at the onset of flow limitation when the upper airway collapses. $P_{CRIT}$ may be expressed as: $P_{CRIT}=P_{IN}-P_{OUT}$ where $P_{IN}$=pressure inside the upper airway at the moment of airway collapse; and $P_{OUT}$=pressure outside the upper airway (atmospheric pressure).

$P_{CRIT}$ is a measure of the severity of upper airway obstruction during sleep, and ranges from a level significantly below atmospheric in normal individuals to levels near or above atmospheric as upper airway obstruction progresses from snoring to hypopneas (abnormally shallow breaths), and ultimately to apneas (abnormal cessation of breathing).

$P_{IN}$ is increased by increased soft tissue mass around the upper airway, particularly during sleep when tissue supporting mechanisms fail in some individuals. This has the effect of compressing the upper airway, and increasing the likelihood that $P_{CRIT}$ will be reached.

The current state of the art in treating OSA involves the life-long use of mechanical systems that pump air (sometimes enriched with oxygen) into the upper airway via a mask that fits tightly over the nose, mouth or both. This pressurized jet of Positive Airway Pressure (PAP) counteracts upper airway collapse by forcing air in to increase $P_{OUT}$ relative to $P_{IN}$ thereby restoring the negative value of $P_{CRIT}$.

This technology is effective, but has the disadvantages of being expensive to purchase and maintain, and many patients find it uncomfortable and impractical to use. The overall long-term compliance with PAP is low, and usually only those with the most severe symptoms continue treatment beyond one year.

OSA can be reversed by major weight loss, but this rarely happens without stomach reduction or bypass surgery that is usually reserved for the most obese patients. Consequently, OSA treatment is usually for life. Less radical surgery involves removing the sagging tissues in the nose and throat, and carving away the back of the tongue to create room for airflow. This procedure has been proven to work in only the mildest forms of OSA.

Another treatment approach has been to wear a Mandibular Advancement Device (MAD), a dental prosthesis that prevents airway collapse during sleep by pushing the lower jaw forward to increase the size of the airway. MADs are attractive since they are worn inside the mouth and are more comfortable than CPAP, but again mild cases respond best. However, MADs may be uncomfortable, cause pain, or even injure the jaw and shift teeth. They usually require custom fitting and adjustment by an experienced dentist, making them costly. They are not a viable option for those patients with multiple missing or diseased teeth.

An urgent need remains for lower cost, safe, effective, controllable and comfortable treatment modalities for snoring and obstructive sleep apnea.

It is recognized by the inventors that a wide variety of other diseases and disorders are amenable to hydraulic pressure therapy delivered so as to promote health and alleviate disease and discomfort, whether it takes the form of suction, traction or tension singly or in combination applied against one or more body parts.

SUMMARY OF THE INVENTION

The invention includes in various embodiments a walled enclosure with at least one distensible membrane spanning its perimeter (or lesser portions thereof), and at least one hydraulic fluid chamber within the enclosure. The walled surface may vary in shape depending on the application. For example, it would be cylindrical in one embodiment to enclose a limb, or trapezoidal in another for application to a torso. In another embodiment the walled surface defines a dome-shaped hydraulic fluid retaining structure with a flexible membrane covering the aperture to which the structure opens. The device is applied with the membrane over a body part, either directly, or indirectly (for example hookably, stickingly or screwably over a protective material, such as an adhesive drape and the like), so that when hydraulic fluid is circulated within the device the resulting positive, negative or traction pressure upon the skin and underlying tissues provides a beneficial effect.

In embodiments of the invention, traction mechanisms are provided for application of therapeutic force, such as pulling tissue, for desirable adjustment of anatomic relationships, including without limitation airways in the treatment of sleep apnea and snoring.

In embodiments of the invention, manipulation of position of the hyoid bone provides a useful means for noninvasively and externally maintaining the tongue in an anterior position. The hyoid bone is the only bone in the body without an articulation with another bone, and is therefore suspended in the anterior neck by attachments to ligaments and muscles. The genio-hyoid muscle attaches the hyoid bone to the mandible, whereas the myoglossus muscle among others attaches the tongue base to the hyoid bone.

In embodiments, low magnitude outward and downward traction forces on the skin of the anterior neck and upper sternum have the effect of displacing the skin and underlying soft tissues inferiorly, and indirectly pulling the hyoid bone inferiorly and anteriorly, thereby stabilizing the base of the tongue to which the hyoid is attached.

In one embodiment, the stabilizing effect is particularly pronounced when the subject has his chin extended in the "sniff position", as measured by the increased force required for a person to swallow when in this position.

In embodiments of the invention, a variety of traction devices may be provided to generate a tugging force on the soft tissues of the neck, gently lifting them superiorly against gravity and away from the windpipe as well as stretching them inferiorly when the subject is lying down. This pulling force acts upon the hyoid bone which is connected to the base of the tongue and the skull by strap-like muscles. The traction force has the net effect of reducing the posterior movement of the hyoid bone, thereby stabilizing the tongue to which the hyoid bone is attached, and moving the tongue slightly forward by shortening the genio-hyoid muscle. These actions open the airway, resist the tendency of the tongue to fall back and obstruct the airway, and also increase the tension in the tongue and airway walls thereby reducing the vibrations during sleep breathing that cause snoring.

Such "pulling" force may be applied in conjunction, and without limitation, by external and/or surgical implementation, spring-force applying materials, adhesives, clips, grips, magnets, implants, distance-adjustable spacers and the like.

In one embodiment of the present invention a neck traction device comprises a concave disc, hereinafter referred to as "disc." The disc is attached to a scaffold by means of a screw mechanism that allows retraction and extension of the disc.

In other embodiments, other shapes may be provided as an alternative to scaffold, and such shapes may accommodate one or more discs therein. In one embodiment, disc may have a diameter of about 3 cm for application to an about 70 kg male. However, other dimensions of manufacture for the disc and scaffold as adapted to other size individuals, including children, or to a particular treatment or body region to be treated, are understood to be encompassed by the present invention. In some embodiments disc and scaffold are constructed of durable plastic material and may be provided in variety of colors, including transparent or translucent material. In non-limiting embodiments, silicone, plastic, rubber and like materials may also be used.

Traction on the skin below the upper airway by the device increases airflow in the upper airway by displacing the hyoid bone and the attached tongue anteriorly, thereby relieving intra-luminal airway narrowing and obstruction.

In embodiments, traction by devices of the invention may be provided in various embodiments by the use of magnets, hydraulics or mechanical force. Tissue contact may be accomplished via direct coupling of a number of integrated biocompatible adhesive pads attached to one or more surfaces of the device, or indirect adhesion to the neck skin surface by means of separate biocompatible adhesive pads that contact the skin and provide an interface for coupling with the traction device.

In an embodiment here magnetic attraction provides the traction force, the adhesive material may contain ferromagnetic material or an oppositely charged magnet that will be pulled towards the magnet in the immobile portion of the device, thereby displacing skin tissues.

In an embodiment where hydraulic pressure provides the traction force, the adhesive material can be securely attached to a piston in the device that can be pulled away from the adhesive pad, thereby gently moving neck skin tissues.

In an embodiment here mechanical force provides the traction, the adhesive material will be securely attached to a retractable surface on the device so that when it is pulled away from the adhesive pad, there is beneficial tugging on neck skin tissues.

The beneficial methods of achieving therapeutic tissue traction may vary depending on individual user characteristics. For instance, individuals with relatively large amounts of neck tissue requiring mobilization may benefit from hydraulic and or magnetic devices, whereas in people with less bulky neck tissue, mechanical means of traction application may suffice.

Traction in embodiments of the invention will deliver the airway expansion equivalent of 5-20 cm water positive airway pressure, which is the usual pressure range required to treat snoring and OSA with PAP by overcoming a positive $P_{CRIT}$ value. However, in embodiments the traction device may require relatively less force to alleviate a set level of upper airway obstruction than does the corresponding PAP because the nasal passages are a source of substantial resistance to airflow. In some embodiments, the excursion of the soft tissues of the neck during traction may be in the 2 mm to 10 mm range depending upon the displacement distance required to stabilize the hyoid bone so as to make $P_{CRIT}$ optimally negative. The traction force to treat snoring is calculated to be in about the 0.3 to 3.0 kgf range, and traction force levels of between about 1.0 to over 5.0 kgf may be used to treat sleep apnea. Avoiding skin trauma or pain will be appreciated as a consideration in the traction force to be applied to a particular patient.

In one embodiment of the external airway patency device, the walled surface defines a dome-shaped hydraulic fluid retaining structure with a flexible membrane covering the aperture to which the structure opens. Within the hydraulic fluid chamber is a partition containing uni-directional or multi-directional valves that control the direction and rate of hydraulic fluid flow, and the pressure waveform. The device is applied with the membrane over the anterior upper airway, either directly or indirectly over a protective material, such as adhesive drape and the like, so that when the user is experiencing obstructive breathing, hydraulic fluid is removed from the device resulting in anterior and or inferior traction upon the skin and underlying hyoid bone. This maneuver causes the upper airway to open providing improved breathing.

In embodiments, the external airway patency device may be operated manually and/or electronically.

In another embodiment, an airway patency chin cushion is used independently in the snoring or OSA patient. It is placed underneath the chin and secured to the neck by means of straps, adhesive pads and the like, and is designed to hold the chin up in a favorable "sniff position" to comfortably maintain an open airway during sleep. It also functions as a mouth-closing device to promote nasal respiration over oral breathing that tends to dry the mouth and promote snoring.

In further embodiments, the invention provides for an integral airway patency chin cushion in conjunction with a walled enclosure providing comfortable traction and support for the chin and facilitating opening of the upper airway.

In embodiments, the hydraulic fluid reservoir is located within the airway patency chin cushion, and hydraulic pressure is used to provide the spring force necessary to counteract neck flexion and undesirable neck rotation and mouth breathing. The hydraulic fluid may communicate with that of the neck traction device, or operate independently.

In embodiments, the airway patency chin cushion may be operated manually and/or electronically.

In further embodiments, hydraulic pressure control systems, patient status monitors (such as a breathing monitor adjacent to the nose and/or mouth), and neck flexion and rotation systems are automatically linked and controlled through wired or wireless communication.

In other embodiments, the external airway patency device is integrated into garments worn during sleep, including without limitation tee shirts and other shirts.

In yet other embodiments, the external airway patency device includes springy loops, adhesive strips, neck drapes, neck collars and the like.

In still further embodiments, the invention is adapted for a variety of medical therapies, including vests, wraps and other devices coupling to the body, to provide suctioning, traction and/or compression of desired tissue areas for treating a range of conditions, including but not limited to, respiratory, circulatory, lymphatic, cutaneous and musculoskeletal conditions.

For instance, the invention in one embodiment can be designed as a respiratory vest worn around the chest of patients with obstructive airway breathing disorders such as emphysema and asthma. The hydraulic forces within the vest may augment expiration so as to reduce the amount of trapped air in the lungs and increase tidal volume.

In another embodiment, the hydraulic respiratory vest may be worn by patients suffering from restrictive chest disorders such as severe obesity, and pulmonary fibrosis. In this instance, the hydraulic forces may augment inspiration, thereby increasing the amount of air inhaled against the abnormally high resistance to lung inflation afforded by restrictive chest wall and lung disorders.

In yet another form, the hydraulic respiratory vest may be worn by patients on a mechanical ventilator, whereby hydraulic forces could be applied sequentially to the various lung zones to promote favorable distribution of inhaled oxygen. In cases where hyperinflated lung zones are already present, the vest may be set to place compressive hydraulic pressure on these areas so as to shunt inspired gases to the more underinflated zones. This maneuver may substantially improve a patient's oxygenation in critical care settings. The respiratory vest may be capable of delivering chest percussion therapy to augment secretion clearance by vibrating the hydraulic fluid at an optimal frequency for loosening thick respiratory secretions.

In another embodiment, a hydraulic respiratory vest device of the invention may provide effective automatic chest compressions as part of a cardio-pulmonary resuscitation (CPR) or Advanced Cardiac Life Support (ACLS) effort. The hydraulic chest compression system may administer resuscitative chest compressions of optimal magnitude and frequency when there is no detectable pulse, and stop once a pulse is restored.

In other embodiments, garments made of elastic materials, such as elastane and like materials, are modified to include zones of increased or decreased elasticity for preventive or therapeutic effects by selectively applying traction to targeted body parts. For example, it is well known that emphysema tends to preferentially damage the upper lung fields, while pulmonary fibrosis affects the lower lungs. In embodiments, an elastic vest worn over the torso may selectively apply traction to reduce expansion of the upper lungs in emphysema, or the lower lungs in pulmonary fibrosis, to beneficially redistribute inhaled air to more healthy areas of the lung improving overall lung function.

In embodiments, the hydraulic respiratory vest may be operated manually and/or or electronically.

The invention also has utility in other embodiments as a circulation assist device for the treatment of low output congestive heart failure, and prevention or treatment of impaired blood or lymphatic fluid flow through the extremities in situations where such flow is abnormally impeded by such conditions as arterial atherosclerosis, incompetent venous valves, blood clots and incompetence of lymphatic vessel valves. For example, s circulation assist device of the invention may be used to treat male erectile dysfunction by its utility in causing controlled penile engorgement by hydraulic inhibition of venous return from the cavernous sinuses. In another instance, when worn over the legs a pulsatile hydraulic powered assist device in an embodiment may be used to improve venous return in patients with coronary artery disease or chronic venous insufficiency. In other embodiments, the assist device worn over the chest may reduce intrathoracic pressure by slightly limiting chest wall excursion during inspiration and slightly increasing it during expiration, thereby increasing cardiac ejection fraction in patients with congestive heart failure.

In yet another embodiment, a circulation assist device of the invention may provide effective automatic chest compressions during CPR or ACLS resuscitation. It has been recently recognized that effective cardiac compressions are the cornerstone of successful cardiac resuscitation efforts, and the algorithm for ACLS has repositioned this intervention from third to first in sequential priority.

Best practices recommend 100 compressions per minute each displacing the sternum for 2 inches in depth in order to provide the best coronary and cerebral blood flow during cardiac arrest. This recommendation is technically and physically demanding for the rescuer, and would be best carried out automatically. A hydraulic chest compression system of the invention may beneficially administer resuscitative chest compressions of optimal magnitude and frequency throughout the resuscitation effort, allowing critical care medical staff to focus on other key tasks, as long as there is no detectable pulse, and to stop once a pulse is restored or the resuscitation protocol is terminated.

Successful cardioversion in the setting of cardiac arrest is best achieved in the first 4 minutes after cardiac standstill. In embodiments, an automatic external defibrillator or the required interfaces are integrated into a vest of embodiments of the invention to facilitate cardioversion as soon as possible should it be necessary.

Cooling the body to 32-34° C. for 12-24 hours has been determined to be helpful in mitigating brain damage in cardiac arrest situations. A circulation assist device of the invention may maintain the necessary temperature drop by, for example, cooling the hydraulic fluid by automated release of dry ice or other coolants once a pulseless state is detected.

In other embodiments, a circulation assist device of the invention may function as a ventricular assist apparatus. There are thousands of people with chronic congestive heart failure on the basis of low left ventricular output resulting from cardiac muscle damage from conditions such as hypertension, coronary artery disease, connective tissue diseases and infiltrative cardiomyopathies. A surgically implanted battery operated electronically controlled set of hydraulic pumps transmitting timed pressure wave boosts in systole to the ventricular outflow tracts or aorta via a diaphragm may save lives and improve quality of life.

In embodiments, a circulation assist device of the invention may be operated manually and/or electronically.

In other embodiments, the invention is capable of operating as a wound healing and contaminated body fluid containment device by providing hydraulic suction therapy to open skin wounds. Suction therapy to local blood vessels improves wound perfusion and accelerates healing. Topical antibiotic solutions, topical hyperbaric oxygen, humidification and sterile irrigation liquid for mechanical debridement each stored in specially designed chambers may be automatically delivered to the infected skin on a programmed schedule, and waste fluids safely collected and contained in a separate removable chamber for later disposal.

Another embodiment of the invention includes the use of a hydraulic fluid for use in prevention of pressure ulcers (bed sores or diabetic ulcers). For example, bed-ridden patients could wear garments or diapers containing hydraulic memory foam-type devices that function as "artificial buttocks" that absorb the contact pressure and moisture that would ordinarily damage the skin. The hydraulic fluid may redistribute with gravity and conform to the new shape when the patient is turned on their side.

In embodiments, wound prevention and treatment devices of the invention may be operated manually and/or electronically.

In yet other embodiments, a hydraulic trauma resuscitation device of the invention may be placed over the bleeding wounds of major trauma victims to tamponade further blood loss while collecting lost blood products for storage in a separate compartment containing sterilizing and anti-coagulating medicaments such as antibiotics and heparin to facilitate re-transfusion either in the field or at a medical center. This application may be of particular value on the battlefield in so-called "damage control resuscitation".

In an embodiment, a hydraulic trauma resuscitation device of the invention may rapidly infuse pressurized resuscitative fluids such as normal saline, lactated Ringer's solution, medications and blood products via central and peripheral venous access.

Another embodiment of a hydraulic trauma resuscitation device of the invention includes operating as a hydraulic MAST suit in situations where the victim is in profound hypotensive shock. This embodiment may monitor pressure applied to the tissues and automatically deflate for intermittent pressure relief to prevent tissue injury, or manually notify a health worker via a built-in alarm system.

In another embodiment, a hydraulic trauma assist device of the invention is placed on a traumatized extremity to serve as a splint and/or to cool or warm the injured tissues as needed to best provide relief. For example, one of the most common sports injuries is an uncomplicated inversion ankle sprain for which the treatment is rest, ice, compression and elevation. A hydraulic ankle boot of the invention may be inflated with a fluid such as water to support weight when walking, and further include pockets in embodiments to hold ice packs to comfortably cool the injury and may be included in first aid kits.

Some embodiments of a hydraulic trauma resuscitation device of the invention may incorporate means of warming hypothermic patients by heating the hydraulic fluid or incorporating a warming blanket or electrically controlled thermal layer into the skin contacting surface.

In other embodiments, a hydraulic trauma resuscitation device of the invention may be reconfigured to function as a wound care device that promotes healing of damaged skin by containing the affected area in an enclosure allowing users to hydraulically draw away and safely contain infected body fluids, and to irrigate the skin with cleansing and antimicrobial medicaments. Such device may control the temperature and humidity of the enclosed wound to relieve pain and promote healing. One embodiment of such device would be simple enough to be operated in the home environment, while a more sophisticated version in other embodiment would be used by skilled health workers in an institutional environment.

In embodiments, a hydraulic trauma resuscitation device of the invention may be operated manually and/or electronically.

Another embodiment of the invention relates to partial or full body suits worn to maintain body optimal temperature in situations in which humans are exposed to temperature extremes. In embodiments, hydraulic fluid may be heated or cooled and circulated within a body suit similar to that worn by scuba divers. The outer shell may include one or more materials that are waterproof (or otherwise environmentally resistant to use conditions) while the inner shell that lines the skin surface may include one or more soft, insulating materials, with a thin layer of hydraulic fluid circulating in between.

In other embodiments, a temperature control body suit of the invention may be combined with a body armor suit to provide an integrated thermal control and penetration injury protection system that is functional in a wide variety of extreme environmental and temperature conditions including underwater or in outer space, for use by combat or security personnel, ballistic sportsmen or astronauts.

Partial or full body suits currently serve as protective armor in law enforcement and military applications. The outer shell of suits of embodiments of the invention may be made of Kevlar®, Spectra® Fiber, Twaron® brand materials or other ballistic and stab resistant materials while the inner shell is constructed of a soft insulating material. Sandwiched in between is the hydraulic fluid layer in which sufficient fluid is circulated to provide adequate body temperature control. A suit of the invention may meet or exceed the most current National Institute of Justice Standard "Ballistic Resistance of Body Armor," minimum performance standard.

BRIEF DESCRIPTION OF THE DRAWINGS

FIG. 1 is a sectional perspective view from below of a hydraulic traction airway patency device in an embodiment of the present invention.

FIG. 2 is a relational diagram illustrating an anterior perspective view of a mechanical traction airway patency device for application to a human subject in an embodiment of the present invention.

FIG. 3 is a lateral view of an airway patency chin cushion shown opening a human subject's airway by keeping a human subject's head in a "sniff position" while keeping the mouth closed in an embodiment of the present invention.

FIG. 4 is a lateral view of an airway patency chin cushion with a tray-shaped chin cushion in an embodiment of the present invention.

FIG. 5 is a front perspective view from above of an airway patency chin cushion with a tray-shaped chin cushion in an embodiment of the present invention.

FIG. 6 is a lateral view of an airway patency chin cushion with a dome-shaped chin cushion in an embodiment of the present invention.

FIG. 7 is a front perspective view from above of an airway patency chin cushion with a dome-shaped chin cushion in an embodiment of the present invention.

FIG. 8 is a front perspective view of a traction airway patency invention including a slider-type adjustment and integrated chin cushion applied to an upright human subject in an embodiment of the present invention.

FIG. 9 is a lateral perspective view of a traction airway patency invention including a slider-type adjustment and integrated chin cushion on a recumbent human subject in an embodiment of the present invention.

FIG. 10 is a disassembled exploded view of a traction airway patency device including a slider-type adjustment with an integrated chin cushion in an embodiment of the present invention.

FIG. 11 is a lateral plan view of a traction airway patency device including a slider-type adjustment with an integrated chin cushion in an embodiment of the present invention.

FIG. 12 is a posterior plan view of a traction airway patency device including a slider-type adjustment with an integrated chin cushion in an embodiment of the present invention.

FIG. 13 is a relational block diagram of a traction control system for treating obstructive sleep apnea of a human subject in an embodiment of the present invention.

FIG. 14 is front perspective view of a double looped chin repositioner worn by an upright human subject in an embodiment of the present invention.

FIG. 15 is a lateral view of a double looped chin repositioner worn by a recumbent human subject in an embodiment of the present invention.

FIG. 17 is a perspective view of a respiratory ventilation redistribution and chest compression vest device in an embodiment of the present invention.

FIG. 18 is an anterior view of a respiratory ventilation redistribution and chest compression vest device in an embodiment of the present invention.

FIG. 19 is a posterior view of a respiratory ventilation redistribution and chest compression vest device in an embodiment of the present invention.

FIG. 20 is a schematic view of a single hydraulic fluid chamber in a respiratory ventilation redistribution and chest compression vest device in an embodiment of the present invention.

FIG. 21 is a schematic view of a pressurizing phase in the operational cycle of a single hydraulic fluid chamber in a respiratory ventilation redistribution and chest compression vest device in an embodiment of the present invention.

FIG. 22 is a schematic view of a depressurizing phase in the operational cycle of a single hydraulic fluid chamber in a respiratory ventilation redistribution and chest compression vest device in an embodiment of the present invention.

FIG. 23 is an external view of a hydraulic femoral artery compression device secured in an anatomically preferred location in an embodiment of the present invention.

FIG. 24 is a schematic view of a hydraulic femoral artery compression device augmenting circulation in an embodiment of the present invention.

FIG. 25 is a perspective view of a hydraulic calf venous compression device within a body-contoured housing with an integrated control unit in an embodiment of the present invention.

FIG. 26 is a posterior external view of a hydraulic calf venous compression device placed on a human lower extremity in an embodiment of the present invention.

FIG. 27 is a cut-away schematic view demonstrating the action of a hydraulic calf venous compression device placed on a human lower extremity in an embodiment of the present invention.

FIG. 28 is a lateral view of a hydraulic calf venous compression device placed on a human lower extremity in an embodiment of the present invention.

FIG. 29 is a schematic, external lateral view of a hydraulic calf venous compression device placed on a human lower extremity in an alternative tubular embodiment of the present invention.

FIG. 30 is a longitudinal, cross-sectional schematic view of a hydraulic calf venous compression device in an alternative tubular embodiment of the present invention with the inner tube deflated.

FIG. 31 is a longitudinal, cross-sectional schematic view of a hydraulic calf venous compression device in an alternative tubular embodiment of the present invention with the inner tube inflated.

FIG. 32 is a schematic internal view of the human body demonstrating the anatomic location of a hydraulic left ventricular assist device and control box in an embodiment of the present invention.

FIG. 33 is a schematic view of the human heart demonstrating the anatomic location of an intra-pericardial hydraulic left ventricular assist device in an embodiment of the present invention.

FIG. 34 is a schematic view of the human heart demonstrating the operation of an intra-pericardial hydraulic left ventricular assist device in an embodiment of the present invention.

DETAILED DESCRIPTION OF THE INVENTION

Figure 16:
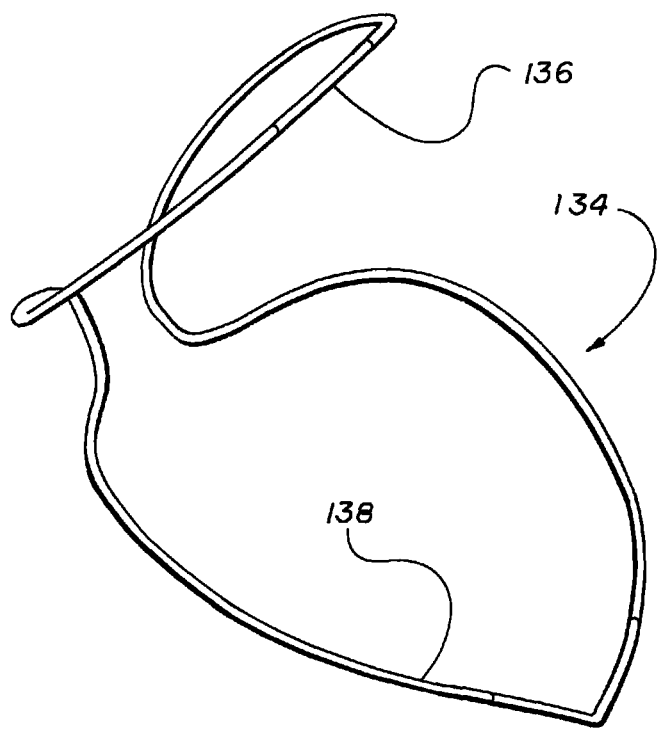
FIG. 16 is a front perspective view from above of a double looped chin repositioner device in an embodiment of the present invention.

The present invention in embodiments provides hydraulic therapy devices and methods through fluid transfer to change the pressure gradient between a membrane and adjacent bodily tissues. Although embodiments for treatment of sleep breathing disorders, including snoring and obstructive sleep apnea, are depicted and described in specific examples, the invention encompasses hydraulic therapy devices and methods for treatment of other medical conditions. In non-limiting examples, the present invention is configurable to a variety of shapes, wraps, vests, garments and the like, for treating internal and external diseases and disorders such as circulatory, muscular, cutaneous, pulmonary and lymphatic conditions. In other embodiments, the present invention provides non-hydraulic devices to couple traction forces to the body, including mechanical and magnetic devices.

In reference to FIG. 1, in one embodiment of the invention fluid in primary chamber 110 is retained between an impermeable membrane 40, such as of a pliable plastic, rubber and similar materials, stretched across an aperture of dome 20 and the inner walls of the primary chamber 110. In a depicted embodiment, the primary chamber 110 is connected to a secondary chamber 120 via an orifice 118 in a partition 115 separating the chambers. In one embodiment, coupling tube 62 provides orifice 60 in secondary chamber 120 as a conduit for hydraulic fluids to be provided into or removed from chamber 120. Coupling tube 62 in such embodiments is connected to a pump or piston to regulate the fluid delivery or removal. Partition 115 assists in regulating fluid flow rates, pressure waveforms and pressure levels through orifice 118 during extraction or introduction of fluid. This regulation mechanism may also include uni- or multi-directional valves 127 positioned within partition 115. In other embodiments, dome 20 may comprise only a single primary chamber 110, or may comprise multiple chambers with multiple partitions and orifices for fluid retention and removal as desired. The hydraulically generated traction force is controlled by the flow of hydraulic fluid through the valves and/or the size of the orifice(s) in the partition 115. Protective padding 30 prevents damage to the underlying tissue. Optionally, in some embodiments, such as shown in FIG. 1, protective padding 30 may include an inner conduit 50 that may be pressure-regulated through coupler tube 50 connected to an air or hydraulic pump or a piston to remove or provide fluids (including gas) for controlling sealing action of padding 30 against the body.

In an alternative embodiment, the dome 20 contains a single chamber without a partition filled with hydraulic fluid with a piston or pump extracting the fluid at a manually or electronically controlled rate and pressure as the means to provide the traction force.

Referring to FIG. 2, an external airway patency apparatus 21 of the present invention may be applied over the superficial tissues of the anterior neck 22. The device is attached to the skin by means of an adhesive pad 23. The skin and attached soft tissues 22 are gently displaced down and out by moving adhesive disc 27 when screw 25 is turned, indirectly directing the hyoid bone and tongue anteriorly thereby relieving occlusive forces that act on the upper airway. The mechanical force responsible for soft tissue traction is adjusted by turning screw 25 attached to the disc 27 that in turn contacts the anterior neck 22. The traction force is dispersed by the scaffold 29 with padded surface area 23 designed to minimize painful compressive pressure generated as a reaction force.

In an alternative embodiment, the adhesive pad is ferromagnetic, and the device retracts the soft tissue by means of a magnet enclosed within the device.

In other embodiments, FIG. 3 depicts an airway patency chin cushion integrated as part of traction device 10 and applied on a subject designed to optimize upper airway opening by adjusting neck position to maintain the optimal "sniff position" and maintaining mouth closure. The chin cushion increases the angle x° between the sternum and the tip of the chin from acute to slightly obtuse.

Referring to FIG. 4, in alternative embodiments traction device 10 includes a chin rest portion 45, such as made of a cushion material 41 to comfortably support the chin of a sleeping patient and promote airway patency by optimizing neck position and minimizing movement of the lower jaw. A chin rest 45 may include extended portions from scaffold 43, as well as in other embodiments one or more cushioned portions coupled over a dome-shaped surface 20 or other walled structure that rests adjacent to a patient's chin. The chin rest may be integral to a traction device, or may be an ancillary attachment removeably coupling to the traction device, including but not limited to hook and loop attachment and other non-limiting connection means.

Referring to FIG. 4, in alternative embodiments traction device 10 is secured with a securing strap 49 around the neck, and includes a tray-shaped chin rest portion 45, such as made of a cushion material 41 to comfortably support the chin of a sleeping patient and promote airway patency by optimizing neck position. Strap 49 is used to snugly and correctly position the device.

FIG. 5 depicts strapless version of traction device 10 with a tray-shaped chin cushion that is secured to the patient using adhesive materials under protective pad 30.

FIGS. 6 and 7 show dome-shaped embodiments of the chin cushion invention 45 as a component of device 10 that is applied to the human body as shown in FIG. 4. The chin support 45 in device 10 takes a dome shape with an attachment strap 49 shown in FIG. 6. FIG. 7 depicts a strapless embodiment with an adhesive attachment beneath protective pad 30. These embodiments also position the neck and mandible so as to optimize neck extension and prevent mouth opening, therefore maximizing oropharyngeal airway size. The upper portion of the chin support is designed to exert a spring force against the weight of the chin to deter flexion of the neck and downward lower jaw motion, and to actively promote healthy neck extension.

In alternative embodiments, mechanical and magnetic forces may be applied singly or in combination with suitable skin attachment interfaces for desired traction of skin and tissues.

FIGS. 8-12 are views of the invention in a magnetic embodiment. The traction device 88 includes a bar 83 (FIG. 10) stickably applied to the skin via adhesive zone 94 and containing in its mid-section a permanent or electromagnet 111. The adhesive bar has a post 105 that allows it to interlock with nut 107 across a longitudinally oriented groove 96 within a brace 129 comprising an upper integrated chin rest 87 and a permanent or electromagnet 112 located within its lower section. The assembled device is positioned down the neck in the midline, with the chin comfortably resting on the chin support 87 so that the device spans the distance from the chin down to the sternum just below the sternal notch as shown in FIG. 8 and FIG. 9.

With specific reference to FIGS. 10-12, in one embodiment of the invention electromagnet 111 located within the adhesive bar 83 has the opposite magnetic charge as electromagnet 112 retained within the base of the brace 129 that has been immobilized by securing the attachment nut 107. In a depicted embodiment, electromagnet 111 confined within the adhesive bar 83 is attracted by immobile electromagnet 112 in the base of the brace 129, creating a magnetic traction force on the skin and opening the upper airway. The magnetic attraction between the electromagnets is adjustable, thereby allowing titration of the traction force required to overcome airway narrowing and closure. The integrated chin rest optimizes neck and lower jaw position for maintaining airway patency.

In other embodiments of the invention, the adhesive bar and brace may contain multiple moveable permanent and/or electromagnets, and their force is adjustable as desired.

In other embodiments, the adhesive bar has an internal mechanical traction control mechanism such a spring coil, cog mechanism and the like. The integrated chin rest is constructed of vibration and/or sound attenuating material to muffle snoring, and also has a springy quality that acts to keep the chin at least perpendicular to the sternum. Electronic circuitry determines the power of the attractive electromagnetic force applied on the ferromagnetic substance.

In another embodiment, the device is placed centrally over the wearer's upper sternum, with the magnets aligned directly over the skin just below the sternal notch. A dome-like structure similar to FIG. 4 covers a ferromagnetic substance located in the central portion of a neck collar. The under surface of this central portion of the collar contacts the skin by means of a soft adhesive cushion made of non-allergenic material, such as but not limited to silicone, attached circumferentially around the perimeter with the central portion made of the ferromagnetic substance. In one embodiment, the ferromagnetic substance may be surgically inserted directly into the skin, while in other embodiments a ferromagnetic adhesive drape provides a protective layer to prevent the underlying skin from being overstretched during traction.

In preferred embodiments, a chin cushion is integrated into the design of traction device 88 in order to achieve maximal airway opening by simultaneously controlling chin position and limiting posterior tongue movement by fixing the hyoid bone in a more anterior position. Chin cushions as depicted in FIGS. 4-7 may be used, and filled with padding materials such as memory foam, silicone gel and the like for the wearer's comfort.

In an alternative embodiment depicted in FIGS. 14-16, chin position is controlled by a double-looped wire chin repositioner 134 that is soft, springy and resists neck flexion to maintain an optimal airway. The upper loop 136 is positioned below the chin, and the lower loop 138 in a more inferior position around the neck. The chin repositioner 134 is covered with soft cushioning material 142 such as silicone rubber, sponge and the like to prevent discomfort to the wearer. This double loop type of chin support inhibits snoring and may be used in isolation or to tether the traction device described with reference to FIGS. 1-12.

In other embodiments of the invention for various medical pressure and traction therapies, devices may include an automatic control system, such as including hardware and software controllers. Pressure and traction devices and their automatic control systems are adapted for the intended application relative to a particular body part. Hardware and software control components may be distributed or centralized into a single control device. In some embodiments, a centralized controller of one or more microprocessors and software control components may be integrated in or on the pressure and traction devices, including the chin rest.

Referring to FIG. 13, in one automated embodiment, three control components are provided for adjusting traction device force of a hydraulic or mechanical traction device 10, including a Breathing Airflow Monitor and Detector 125, a Therapy Responder 126 and a Traction Control 131, collectively referred to as "Control System". It will be appreciated that the functionality of the various components may in alternative embodiments be provided in software and hardware embodiments combining one or more functions.

In one embodiment to relieve sleep disordered breathing, a hydraulic traction device 10 (FIG. 1) is coupled to the Control System. The Breathing Airflow Monitor and Detector 125 assesses the status of cardiovascular, respiratory and other key parameters on a continuous basis. The Breathing Airflow Monitor and Detector 125 also processes biological information received. The Therapy Responder 126 integrates data from Monitor and Detector 125 with preset treatment response algorithms and relays instructions to the Traction Control 131 to implement the treatment protocol by appropriately monitoring and modulating skin tension. In embodiments, the Control Center sends electronic information about the subject to a remote monitoring station such as a hospital, doctor's office and the like.

In an embodiment of the invention utilizing a Control System as depicted in FIG. 13 to treat sleep disordered breathing with traction device, the control components are further described as follows:

1. The Breathing Airflow Monitor and Detector 125 in one embodiment comprises hardware and software components measuring cardio-respiratory parameters such as the depth, frequency and effectiveness of breathing, oxygen and carbon dioxide levels, pulse rate and blood pressure. The instrumentation is able to detect breaths of normal depth and frequency, abnormally shallow or irregular breaths, and abnormal cessation of breathing effort. Nasal pressure transducers and thermistors 122 may be used in embodiments to monitor and report respiratory status. Instruments that non-invasively measure carbon dioxide level (such as an end-tidal carbon dioxide monitor), and arterial oxygen, pulse and blood pressure (such as a pulse oximeter with pulse transit time capability) may be integrated in embodiments. Capability to monitor parameters such as motion, body temperature, electroencephalogram, eye movements, electrocardiogram, muscle tone, respiratory effort, body position, and sound is known to those skilled in the art. The Monitor and Detector 125 may also include a programmed microprocessor discriminating between normal and abnormal parameters such as respiratory, blood pressure and heart rate patterns, and the like. Data is collated in Monitor and Detector 125, and abnormal results passed on to Therapy Responder 126.

3. The Therapy Responder 126 in one embodiment includes a programmed microprocessor responding according to customizable algorithms created based on the nature and severity of the abnormal cardio-respiratory data received from the Monitor and Detector 125. Therapy Responder 126 provides orders to modify traction force as electronically communicated to the Traction Control 131.

4. The Traction Control 131 monitors and sets traction force. A hydraulic regulator 127 moves the skin back and forth by means of a piston or pump removing or delivering hydraulic fluid while traction monitor 129 tracks to provide appropriate traction force from hydraulic traction device 10. Although FIG. 13 depicts regulator 127 as a hydraulic fluid extraction and replacement pressure regulator, it will be appreciated that in other embodiments a Control System may be utilized with other mechanical traction devices (such as traction devices 21 and 88 shown in FIGS. 2 and 10 respectively) and regulator 127 may automatically and mechanically adjust such other traction devices in which traction force monitor 129 measures for application of appropriate force from such device.

In other embodiments, the traction force of a traction device may also be controlled manually, such as by turning the adjustment screw of device 21 in FIG. 2 or sliding a lever of device 88 in embodiments of the invention. Titration of traction force may also be achieved using magnetic attractive force between the skin adhesive patch and disc of device 21 in FIG. 2. Each embodiment of the invention allows accurate and precise control of the traction force and consequently maintaining a negative value for $P_{CRIT}$.

The invention in embodiments has electronic means to store, interpret and transmit data.

In embodiments, prior to falling asleep, the subject with sleep disordered breathing correctly positions the traction apparatus on the neck region and the subject interface components of the Monitor and Detector 125 are attached. When initially applied to the neck before sleep, the traction force on the soft tissues is minimal. When the subject falls asleep and the first abnormal cardio-respiratory data are collected and analyzed by the Monitor and Detector 125, and forwarded to the Therapy Responder 126. When the Therapy Responder 126 determines the response it transmits a command to the Traction Control 131, turning the traction system on, and thereby incrementally reducing luminal upper airway pressure below atmospheric pressure. This process continues until the Monitor and Detector 125 reports complete resolution of upper airway obstruction.

The traction system, such as by a Regulator 127, is turned on and off during sleep as needed to maintain the lowest force necessary to overcome upper airway obstruction. The sensitive and rapid response of the feedback loop between the Monitor and Detector 125 and the Traction Control 131 allows the subject to rest comfortably since large and rapid changes in traction force that may be sleep disruptive are avoided.

The Control System in embodiments is electrically powered with a rechargeable battery, power cord and the like. The Control System can be attached to sensors on the subject's body, and to the traction apparatus using cables, or in other embodiments can communicate using wireless technology, including RF, Bluetooth and the like.

In embodiments, Traction Control 131 physically couples to the traction device. Alternatively, the Control Center can be integrated into the traction device as a single unit.

In other embodiments of the invention, the device is equipped with sound dampening materials and automated mechanisms to minimize snoring noises produced during sleep.

In yet other embodiments of the invention, a traction device may be used as a complement and concurrently with a conventional PAP device, including with an independent or a common automatic control center for coordinated patient monitoring and operation of each device. In such embodiments, the traction device may reduce the pressure requirements of air delivered from the PAP to provide more comfortable therapy to a patient. In other embodiments, a traction device may enhance or improve the effects of PAP use.

In further embodiments, a traction device may be used as a complement and concurrently with breathing strips, oral appliances, such as dental prosthetics and jaw adjustment devices, and/or a like combination of a therapy device(s) with traction device to improve results over conventional use of such devices.

In still other embodiments, FIGS. 17-22 show one type of combined hydraulic respiratory and CPR vest device designed for use in mechanically ventilated patients in whom mismatch of ventilation is common either due to diseased lungs, obstructed airways or recumbent position. A ventilation distribution and automated CPR device 161 is depicted as incorporated into a vest 166 comprising anterior chest pads 163 each positioned over an anterior lobe of the lung, and posterior chest pads 165 each positioned over a posterior lung lobe. The vest 166 is secured to the patient using straps 185 of hook and loop material, clips, buttons and the like.

Each chest pad 163 contains a piston 172 that drives hydraulic fluid 173 to move inflatable hydraulic balloon 175 against the chest wall over well ventilated areas of the lung to selectively limit chest wall excursion, thereby shunting inspired oxygen to less well ventilated lung zones to aid in their expansion. The device 161 is programmable using controller 183 to synchronize inflation and deflation (via wires 177 and hydraulic hoses 187) of one or more hydraulic chest pads so as to best promote oxygen delivery in the critically ill patient.

In the event of a cardiac arrest, the control unit 183 automatically detects loss of a perfusing arterial pulse or cardiac electrical signal, or is manually activated by a health worker. Hydraulic fluid 173 is rapidly shunted via hoses 187 from the anterior chest pads 63 to the anterior CPR unit 192 located over the sternum, and the posterior CPR unit 194 similarly receives hydraulic fluid from posterior chest pads 165. Cardiac compressions are then initiated at the optimal frequency and depth when the two CPR units move towards each other until the resuscitation effort is successful or is terminated.

In obstructive lung diseases such as asthma and emphysema, air is trapped in the lungs due to incomplete expiration, increasing the functional residual lung capacity. Removing this excessive air is accomplished by squeezing the chest between the anterior and posterior chest pads, providing an expiratory assist such that at end-expiration the functional residual lung capacity is reduced to normal.

In restrictive lung diseases due to such conditions as pulmonary fibrosis, respiratory muscle weakness or extreme obesity, the lungs are under-inflated due to incomplete inspiration, reducing the functional residual lung capacity. Increasing the volume of inhaled air is accomplished by pulling the chest out during inspiration when the anterior and posterior chest pads that are adhesively attached to the chest wall are hydraulically pulled or pushed apart, providing an inspiratory assist such that at end-inspiration the functional residual lung capacity is increased to normal.

Other embodiments include an integrated body thermal suit and body armor device This device combines the properties of anti-ballistic body armor with a hydraulic body thermal control device that circulates hydraulic fluid that can be appropriately warmed or cooled to protect the body core from extreme environmental temperatures. This apparatus allows hunters, soldiers and other security personnel operating in high risk ballistic injury situations to deal effectively with concomitant adverse environmental temperatures. A coolant such as dry ice or Freon incorporated into the hydraulic circuit is suitable for cooling, and chemical heating pouches such as those used to warm meals ready to eat (MREs) are suitable for providing body heat.

In other embodiments, a cardiac circulation assist device treats congestive heart failure, angina pectoris, lymph flow abnormalities and peripheral venous stasis by increasing venous blood return to the heart. Venous return, lymphatic flow and cardiac output may all be increased by reducing intrathoracic pressure in persons affected with these conditions. This is accomplished by squeezing the chest between the anterior and posterior chest pads, providing an expiratory assist such that at end-expiration the functional residual lung capacity is reduced. A lower functional residual lung capacity reduces intra-thoracic pressure and increases venous return from the vena cavae, which in turn improves cardiac filling and coronary artery perfusion. This leads to improved circulation and cardiac performance. The respiratory alkalosis caused by this treatment would be corrected by compensatory metabolic acidosis in individuals with normal kidney function.

In other embodiments, such as depicted in FIGS. 23-34, vascular circulatory assist devices that use a hydraulic pressure based system to sequentially compress arterial blood from the heart to the distal extremities (FIGS. 23 and 24), or venous blood and lymphatic fluid from the periphery of an extremity towards the heart (FIGS. 25-31) may be provided. Such apparatuses can be used to treat low output congestive heart failure, arterial insufficiency that causes pain during walking (claudication), to prevent deep venous thrombosis in susceptible individuals, and to treat lymphedema, dependent leg edema and vascular related leg ulcers.

High pressure intermittent pneumatic compression has been shown to improve arterial circulation to the distal extremity by emptying the calf and foot veins of blood, thereby increasing the arterio-venous pressure gradient and reducing peripheral resistance that both cause increased post-compression arterial blood flow to the distal extremity. Compression pressures of 120-140 mmHg for 3-4 cycles per minute in the in at the calf and foot have been found to effectively improve and sustain arterial circulation, exercise performance, ischemic wound healing and quality of life in patients with various degrees of peripheral arterial disease. Hydraulic devices have the advantage of achieving similar results while being smaller in size and quieter in operation allowing them to be used in both mobile and immobile individuals.

In an embodiment, the apparatus 222 of FIGS. 23 and 24 may apply a single augmenting "hammer" pulse, timed to occur in systole by an artery pressure sensor or electrical cardiac signal 256 picked up in the lower limb that acts as a pacemaker. An intermittent hydraulic force is applied to the skin overlying the major arteries 239 supplying an extremity, and increases blood pressure and flow in situations where portions of these blood vessels are diseased by artherosclerosis, which reduces both flow rates through their lumens and the elasticity that is important in maintaining tissue perfusion. The femoral artery 239 has a pulse that may be augmented in the target zone 279 located on the skin of the inner aspect of the lower thigh 227 just above the knee 235 overlying the sartorius muscle in the region of the adductor canal and the vastoadductor membrane. This is because the portions of the femoral arteries proximal to this anatomic site are frequently obstructed by artherosclerotic plaques, causing the femoral pulse to decay to perfusion pressure P1. Artificially boosting the femoral pulse with device 222 to restore normal perfusion pressure P2 beyond target zone 279 just before the take-off of the femoral arteries into the popliteal space behind the knee is highly beneficial to leg perfusion. Piston 272 housed within compression unit 233 and secured to the target zone 279 by strap 231 indirectly compresses hydraulic fluid 273 generating a hydraulic force that acts against the immoveable femur bone 226 thereby augmenting femoral arterial pressure to normal level P2. Device 222 is portable, and may be used while patients are walking to extend their ischemia-free endurance. Retrograde venous flow during arterial compression is prevented or reduced by timing compression of the leg veins just before the arterial pulse pressure augmentation occurs using the electrical cardiac signal detected by reference electrode 256.

Further embodiments of device 222 include manual and battery-powered electronic means of programming the timing and magnitude of the hydraulic force.

In the embodiment depicted in FIGS. 25-28, hydraulic calf venous compression device 244 generates a series of beneficially pressurized and timed pulsatile compression waves from the distal (lower) to the proximal (upper) leg 237 by an array of hydraulic compression units 243 sharing a common body-contoured housing 271 independently programmed electronically using integrated controller 253. Each compression unit 243 cyclically pressurizes and depressurizes a hydraulic chamber placed against the skin along the paths of the major veins 266 targeted for augmented circulation in a similar manner as depicted in FIGS. 19-21. Signals from electrode 256 are used by integrated controller 253 to coordinate the hydraulic compression cycles. Housing 271 is designed to fit comfortably over the calf due to the perimeter seal 238, and is snugly secured to the leg by an adjustable strap 251 that allows the device to remain in place while the patient is walking.

Referring to FIGS. 29-31, another embodiment of the hydraulic calf venous compression invention, device 311 comprises an outer section of flexible tubing 316 (e.g. plastic) through which a much more elastic inner tubing 313 (e.g. rubber) is contained. One or more sections of the outer tubing 316 are resected to expose the inner elastic tubing 313 that then engages the skin of the lower limb. The double tube is wrapped around the leg 237 in a spiral fashion. In this hydraulic embodiment of device 311, a pump 312 forces hydraulic fluid 273 through the inner flexible tubing 313, causing it to bulge outwards in the regions in which the more rigid outer tubing 316 has been cut away so that the inner tubing is in direct contact with the skin. This double tubing system functions as a calf-pump system when fluid 273 (liquid or gas) is sequentially propelled by pump 312 through the inner elastic tube 314 that is initially deflated. As the inner tubing 314 expands, it compresses the soft tissues and veins in the leg against immoveable tibia bone 317 with a peristaltic pressure wave that increases venous return even in people with incompetent venous valves. The anterior part of the leg can be shielded from compression by retaining the outer wall in that area if desired. The fluid is collected in tank reservoir 310 and recirculated to the pump reservoir 312 via return conduit 315. For example, when the pump is turned on, hydraulic fluid 273 is forced through the tubing up the leg towards a tank reservoir 310 located at the top of the device. When the pump is turned off, the fluid remaining in the tubing is forced back into the upper tank reservoir by the force of the contracting inner elastic tubing 313. The fluid can then recirculate to the pump's 312 reservoir passively by gravity, or can be forced down by an accessory pump. A similar action can be achieved with a piston pump as it pumps a bolus of fluid into the inner tubing and up the leg, then stops and reverses direction, and begins to withdraw fluid from the upper reservoir 310 to the pump's 312 lower tank via one-way valves. Sensors such as ECG electrodes or optical sensors can be used to time pumping action with heart rhythm. The entire system may be encased within an appropriate housing with an integrated electronic control box placed around the user's leg or other body location.

The same effect can be accomplished in alternative embodiments using a single section of flat-shaped distensible tubing spiraled around the leg through which gas or liquid is pumped. Since the hydraulic fluid flow moves in a distal to proximal direction toward the heart, it creates a peristaltic pumping action within the veins as each section of the tubing is alternately filled with fluid and emptied. The anterior part of the leg can be shielded if desired.

Additional embodiments include a hydraulic cuff used to measure blood pressure, a biocompatible heart assist system to surround the heart to assist its pumping action, or infusion pumps to infuse medications, nutrients or fluids into humans and or animals, or other pumping systems. The basic embodiment can also be modified by adding fluid lines, valves, sensors, electronics or other components at any point within the system.

In reference to FIGS. 32-34, a cardiac assist device, in this instance a left ventricular assist device 343, may be provided that simulates manual compression of the heart 360 by the human hand. The hydraulic compression pads 351 are strategically placed within the pericardial space 354 between the left ventricular myocardium 361 and the tough fibrous outer pericardial membrane 355, and secured by the surgeon with sutures or staples, or by a self securing mechanism on the fibrous pericardial-facing surface of the compression pad with hooks, clasps, barbs, biocompatible glues and the like.

In another embodiment, several hydraulic compression pads 351 simulating finger tips are surgically secured directly onto the outer layer of the pericardial membrane 355 and are inflated and deflated synchronously during systole and diastole respectively using the EKG or EMG signal from the cardiac leads on the device in contact with the pericardial surface.

Each of the hydraulic pads 351 contains a flexible membrane that pushes against the left ventricular wall 361 to squeeze the wall and augment intra-ventricular systolic pressure during ventricular contraction. In an embodiment, the hydraulic pads 351 are each about the size of a quarter three-dimensionally, and the fluid chamber within each of them containing biocompatible hydraulic fluid (e.g. water) is connected via small hoses and wires 357 to a rechargeable battery-operated controller unit 366 containing a hydraulic pump and electronics embedded under the skin. All the hardware within the body is also made of biocompatible materials such as polyurethane.

The pericardium overlying the left ventricle may be indirectly accessed by a minimally invasive surgical approach under the sternum 363 using thoracoscopic tools. A window may be placed in the pericardium overlying the more easily accessible right ventricle through which thin flat hydraulic compression pads are introduced, and positioned in the pericardial space behind the left ventricle using guidance catheters, magnets and the like.

Alternatively, the pericardium overlying the left ventricle may be directly accessed via a left intercostal approach involving purposely collapsing the left lung.

In other embodiments, the hydraulic compression pads are engineered to detected abnormal rhythms and provide therapeutic electrical currents.

In yet other embodiments, the hydraulic compression pads are designed for placement over the coronary blood vessels 366 to augment arterial supply and/or venous return.

In still other embodiments, the hydraulic compression pads contain a channel for use in coronary artery bypass to replace the autologously harvested grafts currently used to span diseased segments of the coronary arteries.

Those skilled in the art will recognize that the present invention may be manifested in a variety of forms other than the specific embodiments described and contemplated herein. While the invention has been described with reference to the structures and methods disclosed, it is not confined to the details set forth, but is intended to cover such modifications or changes as may fall within the scope of such claims as may be presented.

What is claimed is:

1. An apparatus comprising:
   a pressure therapy first surgically-implantable walled enclosure including two or more hollow chambers separated by at least one partition traversing between walls of the first walled enclosure: at least one valve disposed in the at least one partition separating the two or more hollow chambers in the first walled enclosure;
   a flexible membrane shaped to couple to an internal organ spanning across an aperture defined by a perimeter of the walled enclosure;
   a fluid within the two or more hollow chambers of the walled enclosure;
   a first fluid pumping device coupled to at least one of the two or more hollow chambers; and
   a fluid pressure regulation device coupled to the first fluid pumping device, wherein the fluid pressure regulation device is operatively coupled to a detector receiving physiological data associated with the internal organ.

2. The apparatus of claim 1, further comprising one or more membranes across one or more apertures defined by a portion of the first surgically-implantable walled enclosure.

3. The apparatus of claim 1, wherein the membrane is shaped to cover a portion of a heart.

4. The apparatus of claim 1, wherein at least a portion of the apparatus includes biocompatible materials.

5. The apparatus of claim 1, wherein the detector collects and reports the received physiological data.

6. The apparatus of claim 1, wherein the first fluid pumping device provides at least one of positive pressure and negative pressure to the at least one of the two or more hollow chambers.

7. The apparatus of claim 1, further comprising a second surgically-implantable walled enclosure that includes two or more hollow chambers separated by at least one partition traversing between walls of the second walled enclosure: at least one valve disposed in the at least one partition separating the two or more hollow chambers in the second walled enclosure, a flexible membrane shaped to couple to an internal organ spanning across an aperture defined by a perimeter of the walled enclosure, a fluid within the two or more hollow chambers of the walled enclosure, and a second fluid pumping device coupled to at least one of the two or more hollow chambers.

8. The apparatus of claim 7, wherein the first fluid pumping devices and the second fluid pumping device provide to their respective two or more hollow chambers at least one of positive pressure and negative pressure.

9. The apparatus of claim 7, further comprising surgical attachments coupled to at least one of the first and second walled enclosures selected from the group consisting of sutures, staples, hooks, clasps, barbs and biocompatible glues.

* * * * *

UNITED STATES PATENT AND TRADEMARK OFFICE
CERTIFICATE OF CORRECTION

| | | |
|---|---|---|
| PATENT NO. | : 8,567,407 B1 | Page 1 of 1 |
| APPLICATION NO. | : 13/406607 | |
| DATED | : October 29, 2013 | |
| INVENTOR(S) | : Anthony P. Kimani Mwangi et al. | |

It is certified that error appears in the above-identified patent and that said Letters Patent is hereby corrected as shown below:

In the Claims
Claim 1 (Column 19, lines 46 and 47 of the published Patent) should read as follows:

1. A pressure therapy apparatus comprising:
a first surgically-implantable walled Signed and Sealed this
Twenty-eighth Day of January, 2014

Michelle K. Lee
*Deputy Director of the United States Patent and Trademark Office*